(12) United States Patent
Hoser et al.

(10) Patent No.: US 7,824,890 B2
(45) Date of Patent: Nov. 2, 2010

(54) ISOTHERMAL AMPLIFICATION OF NUCLEIC ACIDS

(75) Inventors: Mark Jay Hoser, Broadstairs (GB); Christian Kurtis, Bexley (GB)

(73) Assignee: Avacta Group PLC, Heslington, York (GB)

(*) Notice: Subject to any disclaimer, the term of this patent is extended or adjusted under 35 U.S.C. 154(b) by 0 days.

(21) Appl. No.: 11/816,356

(22) PCT Filed: Feb. 17, 2006

(86) PCT No.: PCT/GB2006/000578

§ 371 (c)(1),
(2), (4) Date: Apr. 22, 2008

(87) PCT Pub. No.: WO2006/087574

PCT Pub. Date: Aug. 24, 2006

(65) Prior Publication Data

US 2008/0286835 A1    Nov. 20, 2008

(30) Foreign Application Priority Data

Feb. 19, 2005  (GB) ................................. 0503508.4
Feb. 26, 2005  (GB) ................................. 0503988.8
Apr. 5, 2005   (GB) ................................. 0506891.1
Jun. 9, 2005   (GB) ................................. 0511727.0
Oct. 22, 2005  (GB) ................................. 0521570.2

(51) Int. Cl.
*C12Q 1/68* (2006.01)
*C12P 19/34* (2006.01)

(52) U.S. Cl. ................. 435/91.2; 435/6; 435/91.1
(58) Field of Classification Search ................. None
See application file for complete search history.

(56) References Cited

U.S. PATENT DOCUMENTS

| 5,824,517 | A  |   | 10/1998 | Cleuziat et al. |
| 6,251,639 | B1 | * | 6/2001  | Kurn ........................ 435/91.2 |
| 6,399,309 | B1 |   | 6/2002  | Price |
| 2004/0058378 | A1 |   | 3/2004 | Kong et al. |

FOREIGN PATENT DOCUMENTS

| EP | 0497272 A1 | 8/1992 |
| WO | 9949081 A2 | 9/1999 |
| WO | 0120035 A2 | 3/2001 |
| WO | 0236821 A2 | 5/2002 |

* cited by examiner

*Primary Examiner*—Young J Kim
(74) *Attorney, Agent, or Firm*—Rothwell, Figg, Ernst & Manbeck

(57) ABSTRACT

A process of amplifying a nucleic acid template dependent on partial destruction of primer molecules which have extended onto the template molecule followed by strand invasion of the partially destroyed primer template by a replacement primer. The destruction of the primer molecule may be performed by either endonuclease or exonuclease digestion. A signal generation from the amplified products may be obtained by the use of adaptors capable of binding probe molecules as well as the amplified product.

17 Claims, 9 Drawing Sheets

ISOTHERMAL AMPLIFICATION OF NUCLEIC ACIDS

This application is a 371 filing of PCT/GB2006/000578, filed Feb. 17, 2006, which claims priority from GB 0503508.4, filed Feb. 19, 2005, GB 0503988.8, filed Feb. 26, 2005, GB 0506891.1, filed Apr. 5, 2005, GB 0511727.0, filed Jun. 9, 2005, GB 0521570.2, filed Oct. 22, 2005. All of these applications are incorporated herein by reference.

FIELD OF THE INVENTION

The invention relates to the amplification of nucleic acids, in particular to a process of amplifying a nucleic acid template dependent on partial destruction of primer molecules which have extended onto the template molecule followed by strand invasion of the partially destroyed primer template by a replacement primer.

The invention also relates to a method of signal generation from the amplified products.

BACKGROUND OF THE INVENTION

Within nucleic acid and genetic material technologies, it is often necessary to determine whether a gene, a part of a gene, or a nucleotide sequence is present in a living organism, a cellular extract of this organism, or a biological sample. Since any gene or part of a gene is characterized by a specific sequence of nucleotide bases, it is only necessary to search directly for the presence of all or part of said specific sequence in a sample containing a mixture of polynucleotides.

There is enormous interest in this search for specific polynucleotide sequences, particularly in detection of pathogenic organisms, determination of the presence of alleles, detection of the presence of lesions in a host genome, or detection of the presence of a particular RNA or modification of a cell host. Genetic diseases such as Huntington's disease, Duchenne's disease, phenylketonuria, and beta thalassemia can thus be diagnosed by analyzing nucleic acids from the individual. Also it is possible to diagnose or identify viruses, viroids, bacteria, fungi, protozoans, or any other form of plant or animal life by tests employing nucleic probes.

Once the specific sequence of an organism or a disease is known, the nucleic acids should be extracted from a sample and a determination should be made as to whether this sequence is present.

Various methods of nucleic acid detection have been described in the literature. These methods are based on the properties of purine-pyrimidine pairing of complementary nucleic acid strands in DNA-DNA, DNA-RNA, and RNA-RNA duplexes. This pairing process is effected by establishing hydrogen bonds between the adenine-thymine (A-T) and guanine-cytosine (G-C) bases of double-stranded DNA; adenine-uracil (A-U) base pairs can also form by hydrogen bonding in DNA-RNA or RNA-RNA duplexes. The pairing of nucleic acid strands for determining the presence or absence of a given nucleic acid molecule is commonly called "nucleic acid hybridization" or simply "hybridization".

The most direct method for detecting the presence of a target sequence in a nucleic acid sample is to obtain a "probe" whose sequence is sufficiently complementary to part of the target nucleic acid to hybridize therewith. A pre-synthesised probe can be applied in a sample containing nucleic acids. If the target sequence is present, the probe will form a hybridization product with the target. In the absence of a target sequence, no hybridization product will form. Probe hybridization may be detected by numerous methods known in the art. Commonly the probe may be conjugated to a detectable marker. Fluorescent or enzymatic-markers form the basis of molecular beacons, Taqman and other cleavable probes in homogeneous systems. Alternatively the probe may be used to capture amplified material or labelled such that the amplicon is detected after separating a probe hybridized to the amplicon from non-hybridized material.

The main difficulty in this approach, however, is that it is not directly applicable to cases where the number of copies of the target sequence present in a sample is small, less than approximately $10^7$ copies. Under these conditions it is difficult to distinguish specific attachment of a probe to its target sequence from non-specific attachment of the probe to a sequence different from the target sequence. One of the solutions to this problem consists of augmenting the detection signal by a preliminary technique designed to specifically and considerably increase the number of copies of a target nucleic acid fragment if it is present in the sample. A technique of this type is currently called an amplification technique.

The articles by Lewis (1992, Genetic Engineering News 12: 1-9) and Abramson and Myers (1993, Curr. Opin. Biotechnol. 4: 41-47) are good general surveys of amplification techniques. The techniques are based mainly on either those that require multiple cycles during the amplification process or those that are performed at a single temperature. Cycling techniques are exemplified by methods requiring thermocycling and the most widely used of this class of technology is PCR (polymerase chain reaction, U.S. Pat. Nos. 4,683,195, 4,683,202, and 4,800,159; European Patent No. 0 201 184) which enables the amplification of a region of interest from a DNA or RNA. The method usually consists of three steps:

(i) dissociating (denaturing) a double-stranded DNA into single-stranded DNAs;

(ii) annealing a primer oligonucleotide to the single-stranded DNA; and (iii) synthesizing (extending) a complementary strand from the primer in order to copy a region of a DNA of interest.

After this process is completed the system is heated which separates the complementary strands and the process is repeated. Typically 20-40 cycles are performed to amplify genomic DNA to the extent that it can be Her analysed.

Variants of this process include repair chain reaction (RCR) (WO 90/01069) and reverse transcription-PCR (RT-PCR) (Trends in Biotechnology, 10:146-152 (1992)). Alternatively, in a reaction designated as "the shuttle PCR" (Tanpakushitsu Kakusan Kouso, Bessatsu, Protein, Nucleic Acid and Enzyme, Supplement, 41(5): 425-428 (1996)), two of the three steps, that is, the step of annealing the primer and the step of extending are carried out at the same temperature. The ligase chain reaction is an additional technique requiring multiple thermocycles and essentially copies the probe supplied to the system without amplifying target DNA.

A second class of amplification techniques, known as isothermal techniques, are those that are performed at a single temperature or where the major aspect of the amplification process is performed at a single temperature. In the sense that these reactions are performed under isothermal conditions they are more closely related to the subject of the current invention. In common with PCR, the isothermal techniques also rely on the ability of a polymerase to copy the template strand being amplified to form a bound duplex. In the multi-step PCR process the product of the reaction is heated to separate the two strands such that a further primer can bind to the template repeating the process. Conversely, the isothermal techniques rely on a strand displacing polymerase in order to separate/displace the two strands of the duplex and re-copy the template. This well-known property has been the subject of numerous scientific articles (see for example Y. Masamute and C. C. Richardson, 1971, J. Biol. Chem. 246, 2692-2701; R. L. Lechner et al., 1983, J. Biol. Chem. 258, 11174-11184; or R. C. Lundquist and B. M. Olivera, 1982, Cell 31, 53-60). The key feature that differentiates the isothermal techniques is the method that is applied in order to initiate the reiterative process.

Broadly isothermal techniques can be subdivided into those methods that rely on the replacement of a primer to initiate the reiterative template copying and those that rely on continued re-use or de novo synthesis of a single primer molecule.

One known process involving primer re-use is strand displacement amplification (SDA) (G. T. Walker, U.S. Pat. No. 5,455,166), in which a target nucleic acid sequence (and a complementary strand thereof) in a sample is further amplified after initial primer extension by displacement of the synthesised product by a strand displacing DNA polymerase. The strand displacing polymerase gains access to the template strand of the DNA at a site where the primer has been nicked by a restriction endonuclease. The method requires four primers, two of which should be designed to contain a recognition site for the restriction endonuclease.

Where amplification processes rely on primer replacement then the primer which is being replaced must be removed. Numerous methods have been described for primer removal during amplification. Whereas one method relies on the action of a DNA helicase to separate the extended primer from the template (US20040058378A1: Helicase dependent amplification of nucleic acids), other methods rely on the destruction of the primer by a nuclease. Clearly where a nuclease is utilised for primer destruction, the template being amplified must be protected from the action of the nuclease or the nuclease must be directed to specific elements unique to the primer itself.

European Patent No. 0 500 224 describes an exonuclease-mediated strand displacement amplification method which relies on an double strand specific 5'-3' exonuclease that cleaves the extended primer. In this example a modified nucleotide triphosphate must be used within the reaction such that the copied template is resistant to digestion. The consequence of this schema is a non-exponential process.

Numerous primer replacement techniques rely on RNA/DNA composite primers wherein the primer may be removed by the application of the RNA/DNA hybrid specific enzyme RNAse H as exemplified by N. Kurn (WO0120035A2). This technology explicitly describes a linear amplification that does not include any reverse copying of the product strand and is therefore clearly distinguished from the current application. The isothermal amplification method as described by P. Cleuziat in U.S. Pat. No. 5,824,517 is a DNA amplification method that uses four primers at least two of which are chimeric, being composed of a 5' RNA and a 3' DNA element. The technique relies upon the four primers being in an overlapping, nested configuration to produce exponential amplification. An RNAse destroys the 5' RNA element of the chimeric inner primers. This exposes the template strand such that the partially destroyed, extended inner primers are displaced by binding and then extension of the outer primers.

WO 99/49081 describes a method of amplifying DNA in which a duplex specific 5'-3' exonuclease is used to partially digest a primer once it has bound to the template and extended. Thus, after initial binding and extension of a primer, the 5' portion of the primer is destroyed by the 5'-3' exonuclease, which allows a second, shorter primer to bind the exposed single-stranded template DNA. This process allows for exponential expansion of the template population but has an absolute requirement for the use of four primers in an overlapping nested configuration because a shorter primer (similar to the 5' (digested) end of the original primer) is needed such that it wholly binds to the exposed template in order that the strand displacing polymerase may extend from the new primer and displace the initially formed product. Accordingly this technique makes use of two 'full length' primers (forward and reverse) and two shorter primers (forward and reverse) having sequence homology with the partially digestible regions of the 'full length' primers.

It is an object of the present invention to provide an alternative isothermal nucleic acid amplification technique.

It is a further object of the present invention to provide an exponential nucleic acid amplification technique.

It is a further object of the present invention to provide a nucleic acid amplification technique which requires only two primers.

SUMMARY OF THE INVENTION

The present invention thus provides an isothermal process for exponentially amplifying a single stranded nucleic acid template comprising the following steps:

(a) applying a forward primer (primer-1) to the 3' region of the template;

(b) extending said primer by a polymerase;

(c) removing or degrading the 5' terminus of said primer to leave a partly degraded duplex product (product-1);

(d) applying a further primer-1 molecule (primer-1a) to the region exposed by degradation of the 5' terminus of the extended primer (primer-1) so that the 5' region of said further primer (primer-1a) binds to the template;

(e) allowing strand invasion of product-1 by the 3' terminus of said further primer (primer-1a), whereby the 3' terminus of said further primer hybridises with the template in place of the 5' terminus of product-1;

(f) extending said primer-I a by a strand displacing polymerase causing release of product-1 (amplicon) from the template;

(g) reacting product-1 with a reverse primer (primer-2) which binds to the 3' region of product-1;

(h) repeating steps (b) to (g) where the forward primer (primer-1) is replaced by the reverse primer (primer-2) in order to produce product-2 (amplicon);

wherein the original template is re-created by the reaction between product-2 and the 3' terminus of primer-1, whereby the 5' terminus of the primer is extended onto by the 3' terminus of the template.

The amplification method of the invention depends on the replacement of primer oligonucleotides as described above. In common with known processes of this class, the present invention relies on the partial destruction of the primer moiety. However, in contrast to these processes, the present invention provides exponential amplification but demands the use of only two primer elements. The specific differentiating factor that allows for the development of the current technology takes advantage of strand invasion together with the extension of the template copies onto the primer during amplification. In particular, the current method utilises the ability of the original primer to invade the duplex template-product area of the molecule.

Although other techniques are known that rely on only two primers for amplification, these applications only facilitate a linear rather than an exponential process. These methods include exonuclease-mediated strand displacement amplification as described in European Patent No. 0 500 224 and the RNAse H dependent process described above (WO 01/20035). Whereas the method described in WO 01/20035 describes partial destruction of the primer it does not allow copying of the product strand onto the primer. The method defined in EP 0 500 224 utilises only two primers but the complete primer sequence is removed such that only a linear amplification is possible.

This method allows the detection of less than 1000 molecules of nucleic acid and is applicable to a wide range of nucleic acid molecules. Further, it is applicable to diagnostic tests without necessity for thermocycling of the reagents.

The method may also be carried out in a linear manner by using only a single primer.

Preferably, the primers are adapted such that the 5' terminus can be removed or degraded whilst the 3' terminus cannot be removed or degraded. Further, the primers are preferably adapted to bind to the template or product both via the 3' terminus alone and via the 5' terminus alone. In this context, both the destructible primer region and the non destructible region of the primer form independent competent binding units.

Removal or degradation of the primer may preferably be dependent on the primer being bound to the template DNA, for example the primer may be cleaved by a cleavage enzyme selected from a 5'-3' duplex dependent exonuclease or an endonuclease such as a nucleic acid repair enzyme. Preferably the nucleic acid repair enzyme is a DNA glycosylase, such as human oxoguanine glycosylase hOGG1. Preferably the exonuclease is T7 exonuclease. Alternatively, the primer may be cleaved by chemical means.

The polymerase of step (f) has strand displacement activity, whilst the polymerase of step (b) may also have strand displacement activity. Preferably, the polymerase of step (b) and/or step (f) has no 5'-3' exonuclease activity.

If the single stranded nucleic acid template consists of RNA, the method preferably comprises an initial reverse transcription step before step (a).

In one embodiment, the method may be adapted to ultimately rely on a single primer, whereby the method described above is modified such that the reverse primer (primer-2) comprises a region at its 3' terminus which is adapted to hybridise to the 3' end of product-1 and a region at its 5' terminus which has a complement which is adapted to hybridise to primer-1, whereby product-2 contains elements at its 5' terminus and at its 3' terminus that are adapted to react with primer-1 during steps (a) to (g) of the amplification process. Optionally, a further primer (primer-3) is applied to product-1 upstream of primer-2 thereby displacing product-2, primer-3 being adapted so as not to participate directly in the amplification process but to bind to product-1.

The amplified sequence may be detected by a detectable probe which is cognate to the amplified sequence. In one preferred embodiment the method described above further comprises a method of signal generation comprising:

(i) binding an adaptor primer onto the amplicon downstream of the forward primer (primer-1), the adaptor primer comprising a 3' terminus adapted to hybridise to the amplicon, a 5' terminus adapted for use in a signal detection system and a restriction endonuclease recognition sequence;

(ii) extending the adaptor primer onto the amplicon;

(iii) binding the forward primer (primer-1) onto the amplicon;

(iv) extending the forward primer onto the amplicon thereby displacing the extended adaptor;

(v) binding the reverse primer primer-2) to the extended adaptor;

(vi) extending the reverse primer;

(vii) cleaving the extended reverse primer with a restriction endonuclease at the recognition sequence while leaving the adaptor primer intact;

(viii) displacing the cleaved sequence by re-extension of the extended reverse primer from the cleavage site;

(ix) applying a probe which has a sequence capable of hybridising to the complement of the 5' sequence of the adaptor (i.e. the displaced sequence);

wherein binding of the probe to the displaced sequence causes an increase in signal from the probe.

In another aspect, the invention provides a method of signal generation for use during a nucleic acid amplification process comprising:

(i) binding an adaptor primer onto an amplicon, the adaptor primer comprising a 3' terminus adapted to hybridise to the amplicon downstream of a forward primer, a 5' terminus adapted for use in a signal detection system and a restriction endonuclease recognition sequence;

(ii) extending the adaptor primer onto the amplicon;

(iii) binding a forward primer onto the amplicon;

(iv) extending the forward primer onto the amplicon, thereby displacing the extended adaptor;

(v) binding a reverse primer to the extended adaptor;

(vi) extending the reverse primer;

(vii) cleaving the extended reverse primer with a restriction endonuclease at the recognition sequence while leaving the adaptor primer intact;

(viii) displacing the cleaved sequence by re-extension of the extended reverse primer from the cleavage site;

(ix) applying a probe which has a sequence capable of hybridising to the complement of the 5' sequence of the adaptor (i.e. the displaced sequence);

wherein binding of the probe to the displaced sequence causes an increase in signal from the probe.

In another embodiment of these methods of signal generation, the adaptor primer does not contain a restriction endonuclease recognition sequence, but instead the extended reverse primer is displaced by the amplification process described above, i.e. the primer may be cleavable by an enzyme selected from a 5'-3' duplex dependent exonuclease and an alternative endonuclease, such as a nucleic acid repair enzyme. Alternatively, the primer may be cleaved by chemical means. (As shown in FIG. 3.)

In yet another embodiment of the invention signal generation may employ a non-extendable adaptor. In this case the adaptor comprises the same elements as described in other embodiments but the 3' terminus is non-extendible by the action of a polymerase. This can be achieved by blocking the 3' terminus chemically during synthesis as is know in the art or by placing abasic or other entities at or close to the 3' terminus such that extension is disrupted. In this example, signal generation does not rely on the binding of the adaptor to the amplicon during amplification. Rather it relies on the binding of the adaptor to partially extended primers. It is found that some material produced by extension of the reverse primer during amplification is not fully extended. In this context the partially extended reverse primer includes part or all of the amplicon but not the complement of the 3' region of the forward primer. These fragments are able to bind to the said adaptor and extend onto it such that signal generation can be achieved as described above.

In each of these methods of signal generation, optionally, the probe comprises a quencher and a fluorophore and binding of the probe to the displaced sequence results in cleavage of the probe and an increase in fluorescence. The probe may comprise a hairpin structure whereby binding of the probe to the displaced sequence causes opening of the hairpin structure and an increase in signal from the probe.

Optionally the probe may be cleavable by an enzyme selected from a 5'-3' duplex dependent exonuclease or an endonuclease such as a nucleic acid repair enzyme. Preferably the nucleic acid repair enzyme is a DNA glycosylase, such as human oxoguanine glycosylase hOGG1. Alternatively, the primer may be cleaved by chemical means. Preferably the exonuclease is T7 exonuclease.

Cleavage of the probe may increase fluorescence in applications including a quencher and a fluorophore. In addition to this feature cleavage of the probe may cause it to be removed from the sequence to which it is hybridized such that a further probe molecule is able to bind. By this process, the signal generated by the system may be amplified.

Removal of the probe may be induced by the dissociation of its cleaved elements from the nucleic acid to which it is hybridized. By way of example a probe which is hybridized may be 16 base pairs long. Where the probe comprises 8-Oxoguanine moieties spaced four bases apart then after cleavage the fragmented probe comprises elements of 4 base pairs. The system may be implemented such that whereas the full length probe remains hybridised, the smaller fragments will not bind due to their lower melting temperature.

Removal of the probe may be facilitated by partial destruction of its 5' region and consequent strand invasion of the product where the probe comprises elements utilised for nucleic acid amplification described herein. By way of example, the probe may be 16 bases in length and further comprise an exonuclease resistant moiety half way along the length of the probe. Destruction of the 5' region of the probe allows an additional probe to bind and displace the original probe by the process of strand invasion.

The probe may comprise a fluorophore and quencher and further comprise exonuclease resistant elements proximal to the 5' terminus such that its 5' terminus including quencher or fluorophore is cleaved by an exonuclease but where further destruction and removal of the primer inhibited by the exonuclease moieties. In this example the probe will not be removed from its cognate template and a signal will be generated but no signal amplification will be induced.

In another aspect, the invention provides a kit comprising one or more primers for use in the methods described above wherein the primer(s) are adapted such that the 5' terminus can be removed or degraded whilst the 3' terminus cannot be removed or degraded. The kit may further comprise enzymes or reagents for use in the methods described above.

GLOSSARY

Figure 1:
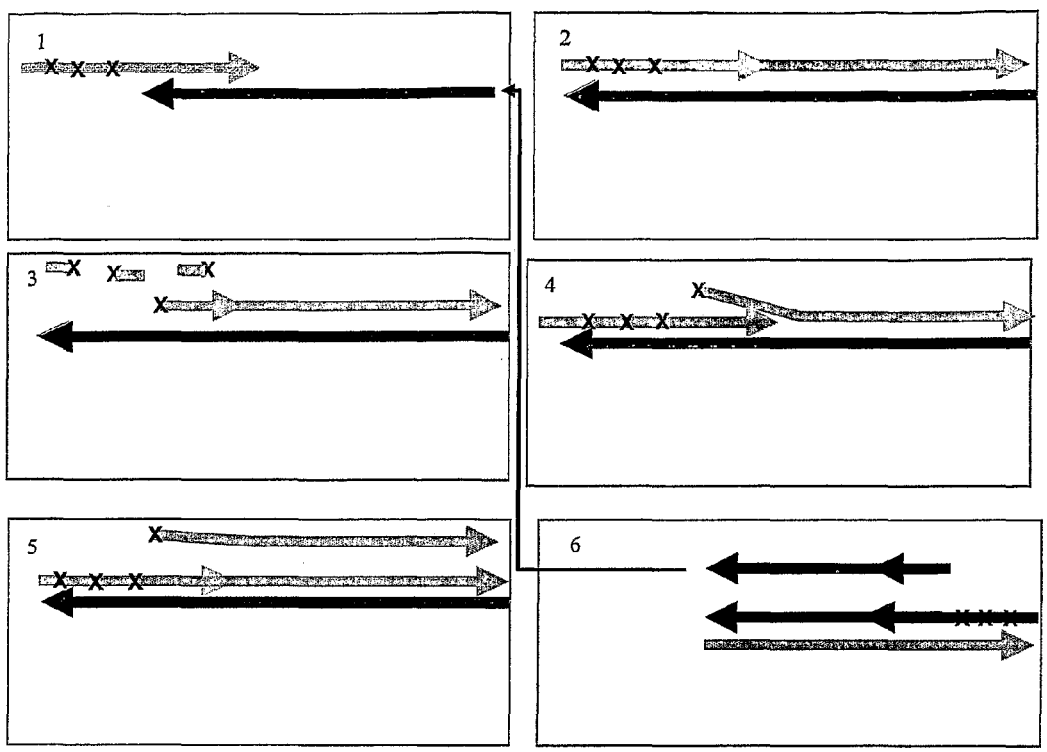
FIG. 1 shows the principal of the amplification process.

The terminology used within this text should be understood in the light of the following definitions.

3' terminus: The area adjoining the ultimate base at the 3' terminus of a polynucleotide. In the context of this invention this includes all of the bases of a primer that are not cleaved during destruction of the 5' terminus of a primer.

5' terminus: The area adjoining the ultimate base at the 5' terminus of a polynucleotide. In the context of this invention this includes all of the bases of a primer that are cleaved or fragmented during destruction of the 5' terminus of a primer.

Abasic: This term refers to a nucleotide that lacks a nucleic acid base. Consequently the nucleotide consists of an open or closed sugar adjoined to other nucleotides by a phosphate bond or without a linkage in its 3' position where it represents a terminal 3' nucleotide.

Adenosine: see Nucleic acid

Alkylation: In the context of the present invention "alkylation" is described as any modification of the nucleoside component of an oligonucleotide that induces a lesion cognate to a specific DNA repair enzyme.

Apurinic: see abasic

Backbone: (nucleic acid) see Nucleic acid

Base: (nucleic acid) see Nucleic acid cDNA: cloned DNA is derived from RNA by the action of a reverse transcriptase.

Cytosine: see Nucleic acid

Downstream: See upstream

Duplex: See Nucleic acid

Endonuclease: an enzyme that is able to cleave internal elements of a polynucleotide/nucleic acid where cleaved moiety is in a specific context.

Exonuclease: an enzyme that is able to cleave the bases from the terminus of a polynucleotide. These bases may be at the 5' terminus or at the 3' terminus depending on the specific exonuclease.

Forward primer: in the context of this invention the forward primer is complementary to or is the same as the 3' terminus of a template or in the case of gDNA it is the primer that initiates the first round of amplification.

Fluorophore: A chemical that absorbs light and then re-emits light at a higher wavelength.

gDNA: DNA derived directly from a genome.

Glycosylase: An enzyme that cleaves the base of a nucleotide.

Guanine: see Nucleic acid.

Helicase: Any enzyme or hetero-complex of proteins that unwinds a duplex nucleic acid exposing single stranded material.

Homologous: A sequence "homologous" to another sequence designates a sequence identical to another or sufficiently identical to hybridize with a sequence strictly complementary to the sequence with which it is homologous.

Heteroduplex: The term "heteroduplex" designates an RNA/DNA hybrid. The term "homoduplex" designates a DNA/DNA or RNA/RNA hybrid.

Isothermal: At a single temperature.

Lesion: See alkylation.

Nucleic acid: A nucleic acid is the molecular entity which is the subject of the present invention. The present invention relates to the amplification of a nucleic acid. In the context of the current invention a nucleic acid may be described as an oligonucleotide or a polynucleotide or as a template. A nucleic acid is a string of nucleotides adjoined by phosphate bonds. The phosphate bonds there for represent the backbone of a polynucleotide. Nucleotides are one of four entities adenosine (A), cytosine (C), guanidine (G) or thymidine (T). Each nucleotide has a back end nominated the 5'/five prime terminus and a front end nominated the 3'/three prime terminus. The front end of each nucleotide is joined to the back end of another nucleotide to form the polynucleotide. Two polynucleotides may sit on top of each other as since an adenosine binds to a thymidine and a guanidine binds to a cytosine. Two polynucleotides can only sit on top of each other if most of the bases bind to the base on the other polynucleotide and if the two molecules are in an anti-parallel configuration. So the back end of one polynucleotide fits onto the front end of another polynucleotide. This process of forming a duplex is called anti parallel binding such that 5'AAGGGCT will bind to 5'AGCCCTT. The longer the complementary polynucleotides then the stronger they will bind to each other and thus melting temperature (Tm)/the temperature needed to separate the strand becomes higher. Each nucleotide comprises a base (A, T, C, or G) as described above and a sugar which hold the base onto the phosphate backbone. Many modifications are possibly within the sugar or base or backbone but where they fit the description above then they are described as a nucleic acid within the current invention. The two major forms of nucleic acid and nucleotides are DNA (deoxyribonucleic acid) and RNA ribonucleic acid. An oligonucleotide sequence is said to be "of the DNA type" if it is made of DNA or if it is a modified polynucleotide sequence that, in addition to the hybridization properties of nucleic acid strands, possesses at least one other property in common with DNA. This common property will of course depend on the functionality of the modified sequence: it is in exercising this functionality that the sequence in question has a property in common with DNA (i.e., behaves like a DNA). An oligonucleotide sequence is said to be of the "RNA type" if is made of RNA or if it is a modified polynucleotide sequence that, in addition to the hybridization properties of nucleic acid strands, possesses at least one other property in common with RNA, namely being sensitive to breakdown by RNAse H under the same conditions as RNA. It is known that RNAse H selectively breaks down the RNA strand of an RNA-DNA hybrid.

Oligonucleotide: See Nucleic acid.

8-Oxoguanine: An alteration in a guanine base of a nucleic acid that occurs naturally resulting from oxidative damage. The alteration causes the base to be copied incorrectly. Consequently numerous repair enzymes have evolved to cleave the base as well as the surrounding backbone of the aberrant portion of a nucleic acid. An example of a repair enzyme with this specificity is oxo-guanine glycosylase.

Primer: designates a single-stranded oligonucleotide structure. These nucleotides can be deoxyribonucleotides and/or ribonucleotides. These nucleotides can be modified. The oligonucleotide primers, once hybridized on a nucleic acid sequence (DNA, RNA or DNA-RNA chimeric molecule) that is substantially complementary are polymerase substrates. The 3'OH end of these substrates can be elongated, in the presence of adequate nucleotides and a polymerase, leading to synthesis of a strand complementary to the template sequence on which said primer is hybridized. A primer can also be constituted by hybridizing the end of a single-stranded nucleic acid sequence on itself, leading in particular to formation of hairpin or stem-loop structures. The oligonucleotide primers hybridized on a nucleic acid sequence have the property of attaching the polymerases to their 3'OH end.

PCR: Polymerase Chain Reaction. This process is the most commonly used method that enables nucleic acid amplification. It is not isothermal.

Polymerase: An enzyme that copies a nucleic acid into its complementary strand. A polymerase copies a template from 5' to 3'.

Replacement primer: In the context of the invention a replacement primer is designated a primer in solution that is used to replace an identical primer bound to a template.

Reverse primer: In the context of this invention the reverse primer is able to bind to the complement of the template that initiates amplification. This complement is the product of forward primer extension.

Restriction Endonuclease: A restriction endonuclease is an enzyme that recognises duplex nucleic acids of a specific sequence, dependent on the particular endonuclease. Consequent to the binding of the endonuclease, one or both strands of the nucleic acid are cleaved. Where only one strand is cleaved, the endonuclease is described as a nicking enzyme.

Strand displacement: The process by which a polymerase separates the strands of duplex nucleic acid in order to access the template strand onto which it is copying.

Strand invasion: Strand invasion is the phenomenon by which a single stranded nucleic acid binds to a duplex nucleic acid displacing one of the strands.

Template: A template represents the oligonucleotide element which contains the oligonucleotide sequence that is amplified by the inventive process. The template may be double stranded or single stranded and in the case of a double stranded oligonucleotide, the two strands are separated prior to amplification. The template may include the complete primer sequence or complement of the primer sequence in the case of the reverse primer. The template may comprise only the 3' non-destructed sequence of the primers. Equally it may cover the complete primer sequences or it may have additional bases upstream of the 5' terminus of its cognate primer regions as is the case with genomic and cDNA.

Upstream: The term "upstream" designates a region located at the 5' end of the nucleic acid or the polynucleotide sequence in question, and the term "downstream" designates a region located at the 3' end of said nucleic acid or said polynucleotide sequence.

DETAILED DESCRIPTION OF THE INVENTION

The present invention affords the opportunity to linearly or exponentially amplify a nucleic acid sequence.

The nucleic acid sequence may comprise DNA, reverse transcribed RNA (cDNA) or genomic DNA. The nucleic acid may also contain modified or unnatural nucleosides where they can be copied by the action of a polymerase.

Essentially, a primer binds to a template and is extended by the action of a polymerase. The primer is destroyed proximal to its 5' terminus (back end) leaving the extended 3' terminus (front end) intact. As a consequence of this process the template strand becomes partly exposed allowing the 5' terminus of another identical or homologous (see glossary of terms) primer (replacement primer) to bind to the template. The 3' terminus of the replacement primer is now in competition with the original (extended) primer for binding to the template. The 3' terminus of the replacement primer is found to invade this region, which is now the 5' terminus of the extended primer, and subsequently, in the presence of a polymerase, the replacement primer extends along the template displacing the original extended primer which includes a complement of the template (the product). The displaced product binds to a reverse primer under the same conditions such that a reverse product is produced and displaced. The reverse product naturally has the same sequence as the original template and also includes a region cognate to the 3' terminus of the original primer that was not destroyed. This reverse product is able to bind an additional forward primer. Notably the reverse product does not include the complement to the 5' terminus of the primer and the initial binding event is between the template and the 3' region (non destructed region) of the primer. The reverse product copies back onto the 5' terminus of the primer and the primer copies onto the template initiating the complete process in a reiterative manner.

One embodiment of the invention comprises the steps of claim 1.

The invention will now be described in more detail with reference to the figures.

FIG. 1 illustrates the principal of the amplification process:

1: The forward primer (primer-1; grey) anneals to the single stranded nucleic acid template (black). The primer contains one or more lesions (X) towards its 5' terminus. These lesions induce cleavage of the primer proximal to the lesion if the primer is in the form of a duplex. An example of such a lesion is 8-oxoguanine in concert with Human 8-oxoguanine glycosylase (hOGG1).

2: The forward primer (grey) extends onto the template (black) by the action of a polymerase (not shown). Equally, where the template is initially shorter that the initiating primer at the primer's 5' terminus, but wholly cognate to its 3' terminus, the template extends onto the 5' terminus of the primer.

3: The 5' terminus of the primer, now in the form of a duplex, becomes susceptible to cleavage, for example by hOGG1, and is cleaved at the positions occupied by the lesion (s). As a consequence an area of the primer 5' to the lesion is fragmented and does not bind to the template due to the reduced affinity of the fragmented part of the primer for the template. The 3' terminus of the primer remains bound to the template due to its length which is also increased by the extension of the primer onto the template further raising the melting temperature of this element.

4: The 5' terminus of an additional primer (primer-1; grey) which is identical to or has similar characteristics to the original primer binds to the template at the region exposed by the fragmentation of the original primer. The 3' terminus of the new primer competes with the 5' terminus of the extended primer (product-1) for binding to the template. The 3' terminus of the new primer is found to invade the pre-existing duplex between the product and template to the extent that it anneals to the template and then extends onto the template. This process results in the displacement of the product-1 (grey).

5: When the new primer becomes fully extended the product-1 is completely displaced and consequently two complementary copies of the original template are made. The new extended primer will also be destroyed in the same fashion as the original primer in a recursive fashion producing multiple copies complementary to the template at a constant rate (linear amplification).

6: Since the complementary copies of the template that have been released are single stranded they are free to react with the second primer (reverse primer; primer-2; black) under the same scheme as outlined in steps 1-5. As a consequence of this reaction each template molecule produces a second identical template molecule during each complete cycle and the amplification consequently becomes exponential.

Figure 2A:
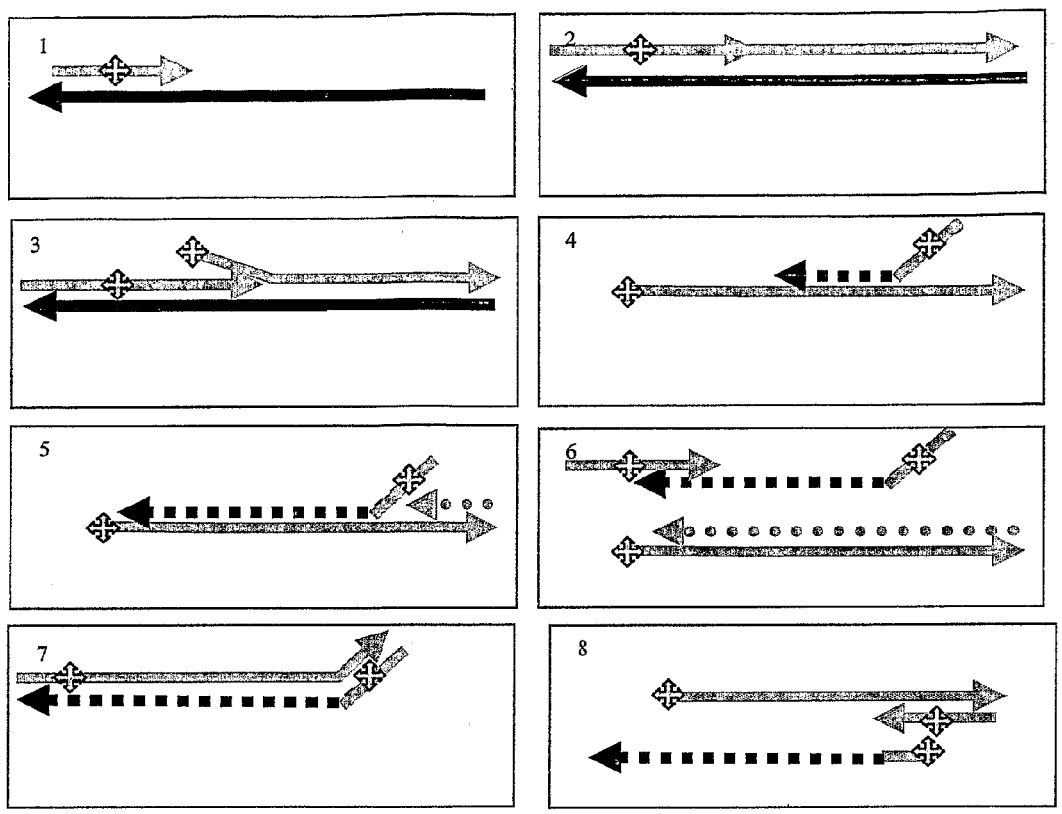
FIGS. 2A and 2B show an amplification process which ultimately relies on a single primer.
Figure 2B:
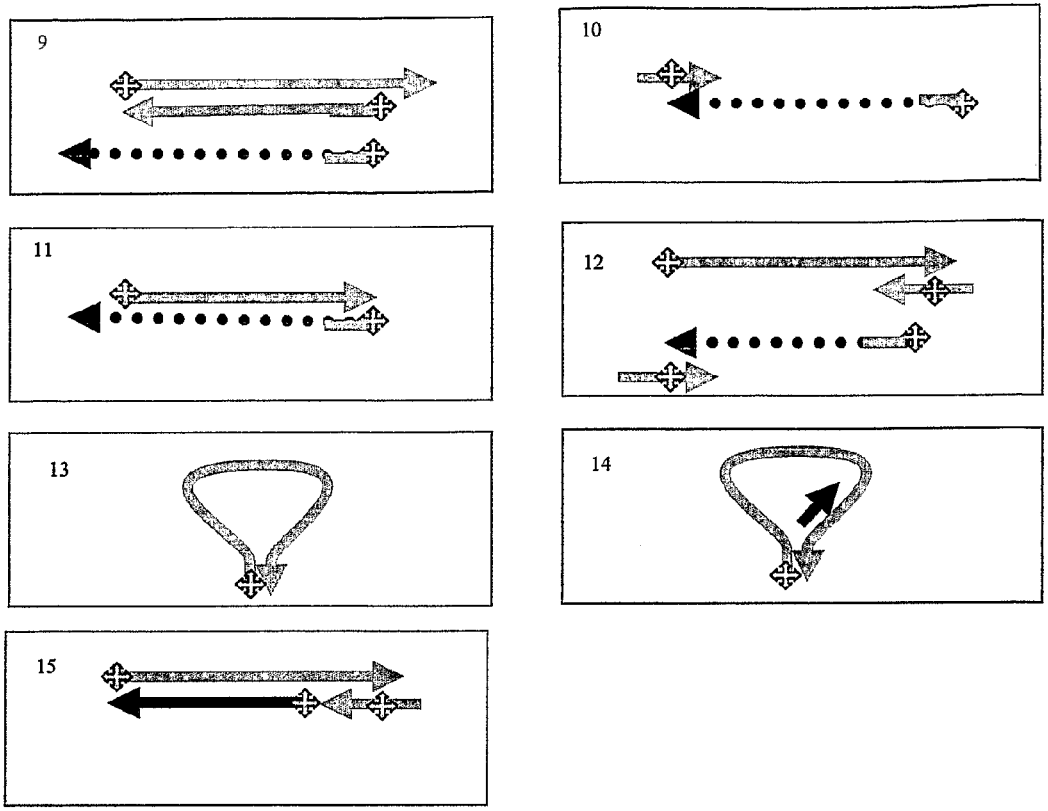

FIGS. 2A and 2B show an amplification process which ultimately relies on a single primer.

1: The forward primer (primer-1; grey) anneals to the single stranded nucleic acid template (black). In this example, the primer comprises a phosphorothioate group (✦) in the middle of its sequence. Equally a lesion based primer may also be applied as an alternative, described in FIG. 1.

2: Primer-1 extends onto the template strand by the action of a polymerase (not shown).

3: As described in FIG. 1, the primer is partially cleaved. In this variant of the invention, the 5' terminus of the primer is cleaved by a duplex dependent 5'-exonuclease and the phosphorothioate group acts as an exonuclease resistant moiety, such that the 3' terminus of the primer is protected from destruction. In this variant no other lesions are needed within the primer. A new primer displaces the partially degraded primer extension product (product-1) by strand invasion and strand displacement, as described above.

4: A reverse primer (primer-2) binds to product-1. In contrast to the system outlined in FIG. 1, the reverse primer comprises a region at its 3' terminus which is cognate to the product (grey line with ✦) but its 5' terminus comprises a region similar to that of primer-1 (dashed line).

5: Primer-2 is extended onto product-1 (grey) producing product-2 (dashed). A third primer (primer-3; dotted line) binds to a position upstream of primer-2 and, as such, it is able to displace product-2 by strand displacement. Primer-3 does not contain any nuclease resistant moieties and as such does not participate directly in amplification.

6: Product-2 is displaced by primer-3. This product-2 now contains elements at its 3' and 5' terminus that can react with primer-1 during amplification, as shown in steps 7 and 8. It should be noted that this system can be extended such that both primer-1 and primer-2 can be designed in a similar way which can induce an amplifiable product using a primer that is not cognate to any aspect of the original amplified region. Primer-1 (grey) binds onto product-2 (dashed).

7: Primer-1 (grey) extends onto product-2 (dashed). Equally, since the template (i.e. product-2) is now shorter that the initiating primer at the primer's 5' terminus, but wholly cognate to its 3' terminus, the template extends onto the 5' terminus of the primer 8: After extension and displacement, the new product (product-3; grey) can also bind to primer-1 (grey).

9: Primer-1 (grey) extends onto the product-3 (grey) to produce product-4 (dotted), which is invaded and displaced by binding and extension of a further primer-1 (not shown).

10: A further primer-1 (grey) anneals to product-4 (dotted).

11: Primer-1 extends onto the template strand by the action of a polymerase (not shown) and the primer is partially cleaved at its 5' terminus by a duplex dependent 5'-exonuclease, the phosphorothioate group acting as an exonuclease resistant moiety, thus protecting the extended product.

12: Thus, a sequence of events is established that allows full exponential amplification from a single primer.

13: Since the products that are released comprise a sequence similar to a primer sequence at its 5' terminus and a sequence that is now cognate to that sequence at its 3' terminus, the stem loop structure shown here may form prior to an additional primer binding event.

14-15: The application of an extendible primer cognate to the loop region may be applied to facilitate opening of the loop in open the loop and facilitate binding of the next primer.

Figure 3A:
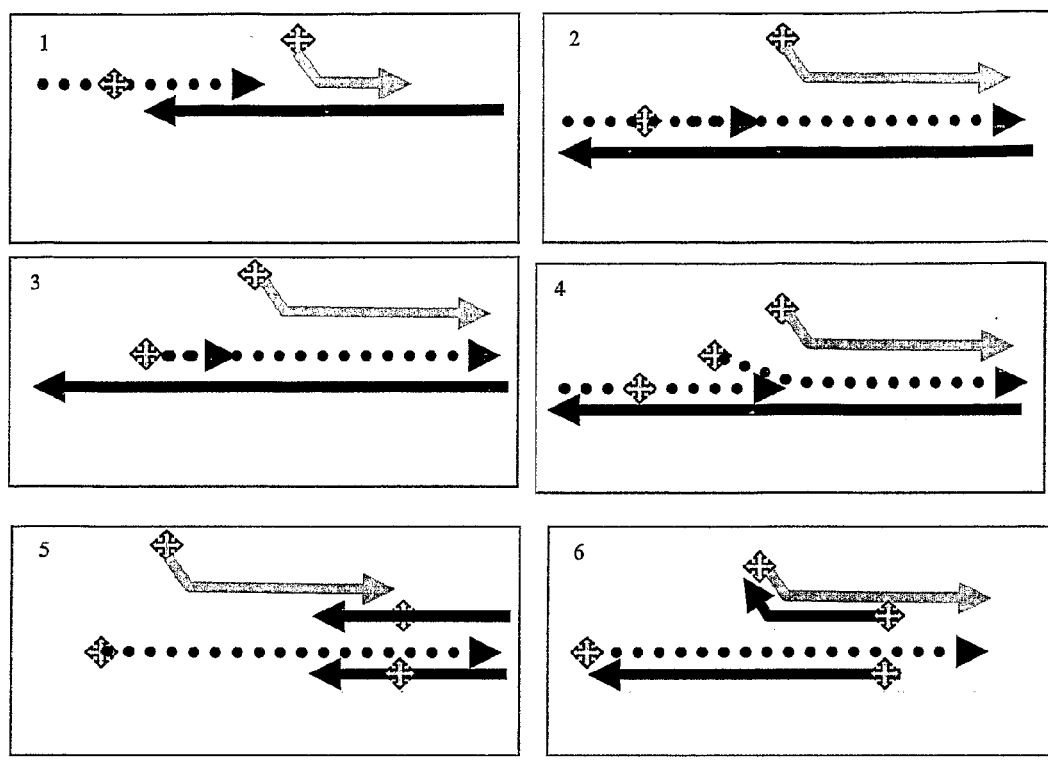
FIGS. 3A, 3B and 3C show isothermal amplification and signal generation using an adaptor primer.
Figure 3B:
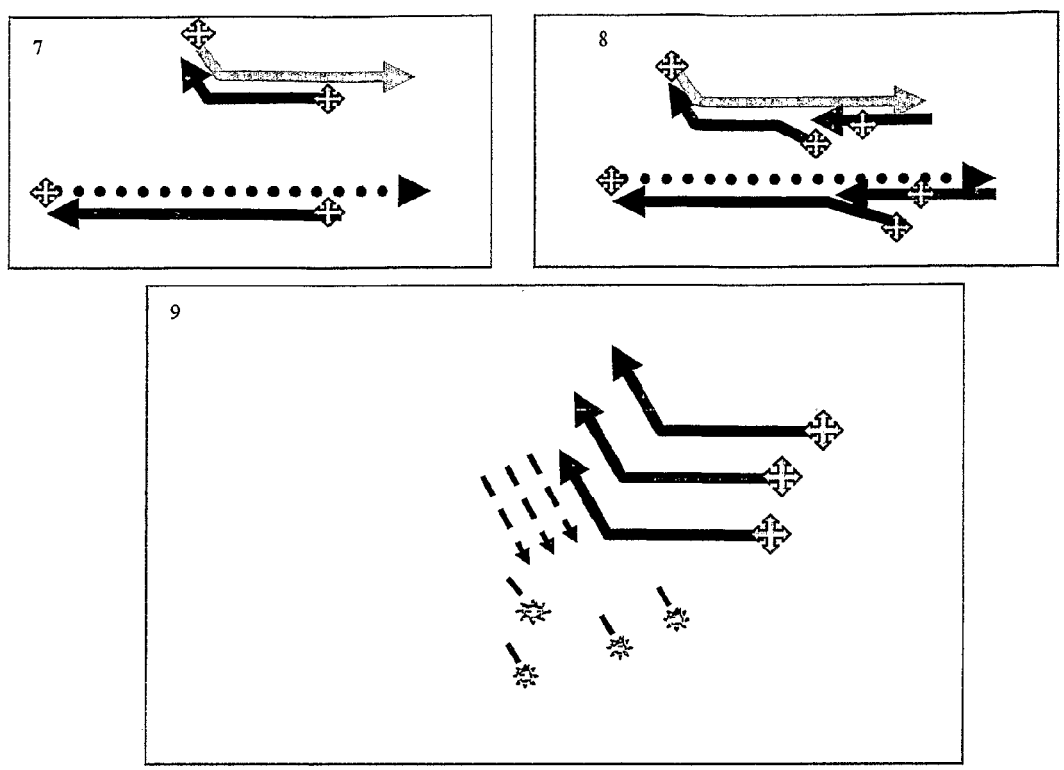
Figure 3C:
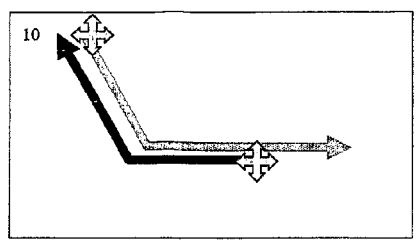
Figure 3C:
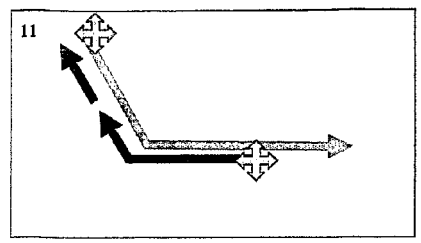
Figure 3C:
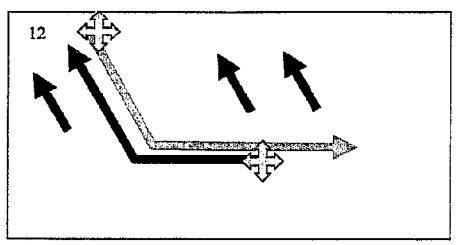
Figure 3C:
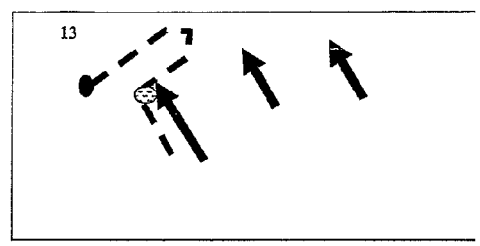
Figure 3C:
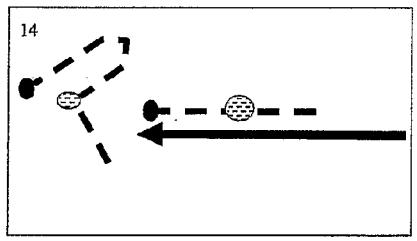
Figure 3C:
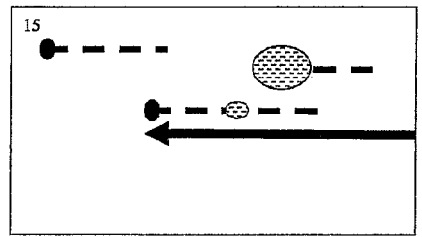

FIGS. 3A, 3B and 3C show isothermal amplification and signal generation using an adaptor primer.

1: A primer comprising a phosphorothioate moiety (✦) at its 5' terminus (primer-1; dotted) is applied to a template (black). (Alternatively, a lesion based primer could be used.) A second primer (adaptor primer; grey) which may not contain any modified elements binds downstream of the original primer. The adaptor primer comprises a 3' terminus that is cognate to the template and a 5' terminus that is not cognate to the template. It may be preferable that the adaptor primer does not directly participate in exponential amplification of the system in order to avoid the possibility of non-template dependent background amplification of the template region to be detected. In this context, the adaptor primer may comprise an oligonucleotide that lacks suitable lesions or exonuclease resistant moieties. Alternatively, the adaptor may comprise exonuclease resistant moieties at its 5' terminus to resist any degradation of the adaptor that could induce participation in amplification as is shown in this figure.

2: Both primer-1 and the adaptor primer extend onto the template but the adaptor is displaced by primer-1. Equally, the template extends onto the 5' terminus of primer-1.

3: The 5' terminus of primer-1 product (product-1; dotted) is cleaved by the 5' exonuclease. The adaptor primer product (product-2; grey) is not cleaved since its 5' terminus is not cognate and is therefore not a substrate for the duplex dependent 5' exonuclease; furthermore its displacement also negates its cleavage.

4: The product-1 is displaced by a further primer-1 binding event.

5: The released product-1 and product-2 react with the reverse primer (primer-2; black). Primer-2 also contains a phosphorothioate moiety (✦) between the 3' and 5' regions.

6-8: The products of the reaction in 5 extend and the 5' terminus of the primers are cleaved. These events result in recursive copying of the template by primer-1 and primer-2 inducing an exponential amplification of the template. In this case, the adaptor primer is non cleavable (it contains phosphorothioates at its 5' terminus) and so exponential amplification of the adaptor does not take place. Rather a single stranded fully cognate complementary copy of the adaptor primer is produced (adaptor complement; black with skewed 3' head region) that may be used in a detection system. The amount of adaptor complement that is induced is therefore dependent on the amount of template copied by primer-1 and primer-2.

9: The adaptor complement may be used for the purpose of detection of amplification as shown below. Since the 3' terminus is not cognate to the template under investigation, it may be designed to fit with a universally applicable detection system irrespective of the specific template under investigation. For example, such systems include a system based on capture of a probe, a lateral flow system, or a quencher-fluorophore system as shown here. The 3' terminus of the adaptor complement anneals to a probe (dashed line). The probe contains a fluorophore and a quencher and an 8-oxoguanine moiety. Once annealed to the adaptor complement, the duplex is cleaved at the 8-oxoguanine moiety by hOGG1, thus separating the fluorophore and quencher elements. Accordingly the fluorescence of the system increases since the cleaved probe is released allowing further probes to bind.

10: In a preferred embodiment of the invention, the primer-2 (black) copies onto the adaptor (grey) as described in 6-8. In this example, the adaptor cannot exponentially amplify due to the inclusion of phosphorothioate moieties at its 5' terminus where an exonuclease is used during amplification. Where a glycosylase is used for amplification then this is not necessary but no substrates for the glycosylase are included in the adaptor. It is important to ensure that the adaptor does not amplify exponentially by the same mechanism inherent in the amplification process since this will minimise amplification based on non-specific interactions between elements of the system.

11: Within the adaptor, upstream of the amplicon binding region a recognition site for a restriction endonuclease is placed. The sequence present in the adaptor is designed such that (in contrast to that used in strand displacement amplification) the duplex adaptor is nicked on its complementary strand which is the opposite side to the original adaptor. The fragment downstream of the nick comprises a sequence with significant complementarity to a probe used for detection.

12: The nicked sequence extends from its 3' terminus which displaces the probe binding element (short black arrow). This induces a further cleavage sequence in the adaptor which is nicked by the restriction endonuclease and the production of probe binding elements continues repetitively.

13: The released probe binding element is able to bind to the probe (dashed line). The probe comprises a signalling moiety whereby the signal is altered consequent to the interaction of the probe and the probe binding sequence. In this case, the probe contains a fluorophore and a quencher which are in close proximity by being on opposite sides of a hairpin in the probe such that the quencher alters the properties of the emitted fluorescence. The fluorescence alteration may be a change in frank fluorescence or other fluorescence properties exemplified by a change in fluorescent lifetime or polarization. Where the signal output is not frank fluorescence then the presence of the quencher moiety may not be necessary. In this case, there is an overhang in the hairpin of a probe which protects against hybridization independent cleavage in systems that rely on 5-3 exonuclease. In other systems such as those that rely on 8-oxoguanine this overhang is not necessary.

14: When the probe binding element extends onto the probe, the quencher is separated from the fluorophore and the fluorescence in the system is increased.

15: The probe may be designed such that it can be destroyed by elements in the amplification system. 8-oxoguanine moieties may be placed into the probe or the probe may be a substrate for a duplex specific 5'-3' exonuclease such as T7-exonuclease. Where this is a feature of the probe then destruction of the probe results in efficient separation of fluorophore from quencher maximally increasing the fluorescence of the system. Cleavage of the probe also enables further probe molecules to bind to the probe binding element such that a degree of signal amplification is possible.

General Considerations for Optimisation of the System.

Balance of Enzymes

Within the amplification schema of the invention primer is consumed as it is incorporated into the product of amplification. Numerous features of the invention may cause primer to be consumed without the production of amplified template.

1: The replacement primer may bind to template and become cleaved prior to invasion of the original primer such that it is removed from the system since it will not be held in place at its 3' terminus.

2: The replacement primer may be cleaved and further replaced after invasion but prior to extension and thus only a partially extended product may be displaced. Where the product has not been extended to the extent that it can bind to a reverse primer then it becomes a non-viable component in terms of amplification.

It is therefore advantageous that various aspects of the system are balanced in favour of amplification. The polymerase is used such that extension of the primer by strand displacement of a product produces a full length amplicon prior to displacement by a further replacement primer. Where the amplicon length is larger, then the concentration of the enzyme used for amplification may be reduced accordingly such that replacement is slowed down allowing time for the polymerase to fully extend the complete product. As such a polymerase with a high degree of processivity and strand displacement is advantageous.

Where primer is consumed prior to invasion then the efficiency of the cleavage enzyme may also be lowered. Equally the efficiency of strand invasion may be increased as discussed below.

The buffer system utilised in the amplification protocol should be compatible with all elements supplied to the system. Clearly optimum conditions for all components may not be achieved within a single buffered system. Numerous opportunities exist that may be used to balance the experimental condition such that the system works efficiently.

Some cleavage enzymes applicable to the current invention may be poorly compatible with a higher salt concentration. By way of example T7-exonuclease is significantly inhibited by concentrations of salt above 50 mM. By adjusting the concentration of this component the system may be optimally balanced.

Primer design also impacts on the balance of the system since alteration in the length and melting temperature of the destructible and or non-destructed aspect of the primer as well as the chosen amplicon length can alter the balance of invasion displacement and binding by enzymatic or buffer component secondarily to other changes.

Design of Primer

The current invention relies on the destruction of a nucleic acid primer at a region proximal to its 5' terminus. Numerous isothermal amplification technologies rely on this process but these technologies either rely on additional primers for exponential aspects of the amplification or only involve a linear expansion of a nucleic acid population with time.

The number of primer nucleic acid bases removed must be enough to enable a further primer to bind to the region exposed by the primer destruction and the number of bases remaining at the 3' terminus must be enough for a new primer to bind to a displaced strand since the displaced strand does not contain the complement to the 5' terminus of the primer. Furthermore the binding of the replacement primer to a partially destroyed primer where it is bound to a template must also invade the 3' terminus of the bound partially destroyed primer. These features are also effected by the ambient temperature of the reaction.

It is not necessary that the melting temperature of the area of the primer binding to the template is above the ambient temperature since the concentration of primer in the system can be increased to above that of the Kd between the elements in order to enhance binding efficiency.

Typically the number of bases exposed at the 5' terminus will be more than eight at an ambient temperature of 37° C. and the number of bases at the 3' terminus that bind to a displaced product will be more than nine at 37° C. Typically this number is increased by one for every three degrees centigrade rise. These features may be impacted by the buffer solution utilised during amplification since various salts and other components may alter the affinity between templates and primers (DNA helix destabilization by Proline and Betaine: possible role in the salinity tolerance process Chadalavada S. V. FEBS Letters 410 (1997) 201-205). Where primer destruction is achieved using an endonuclease then the effect of the lesion placed in the primer as well as the template base that it is cognate to must be considered. Where 8-oxoguanine is the base of choice and its cognate base is a cytosine then the impact of the lesion on melting temperature and consequent alteration on primer length is found to be minimal. Conversely when the oxo-guanine is place opposite to a different base then the impact on the system is more significant and the primer length may need to be extended. Generally the precise and optimal primer length must be established empirically.

Where the 5' terminus of the primer is an RNA then the impact of these bases on primer length is also minimal.

Where the 5' terminus of the primer comprises Uracil or Uracil converted to abasic sites or where it comprises abasic sites directly then the primer length is extended.

Figure 4:
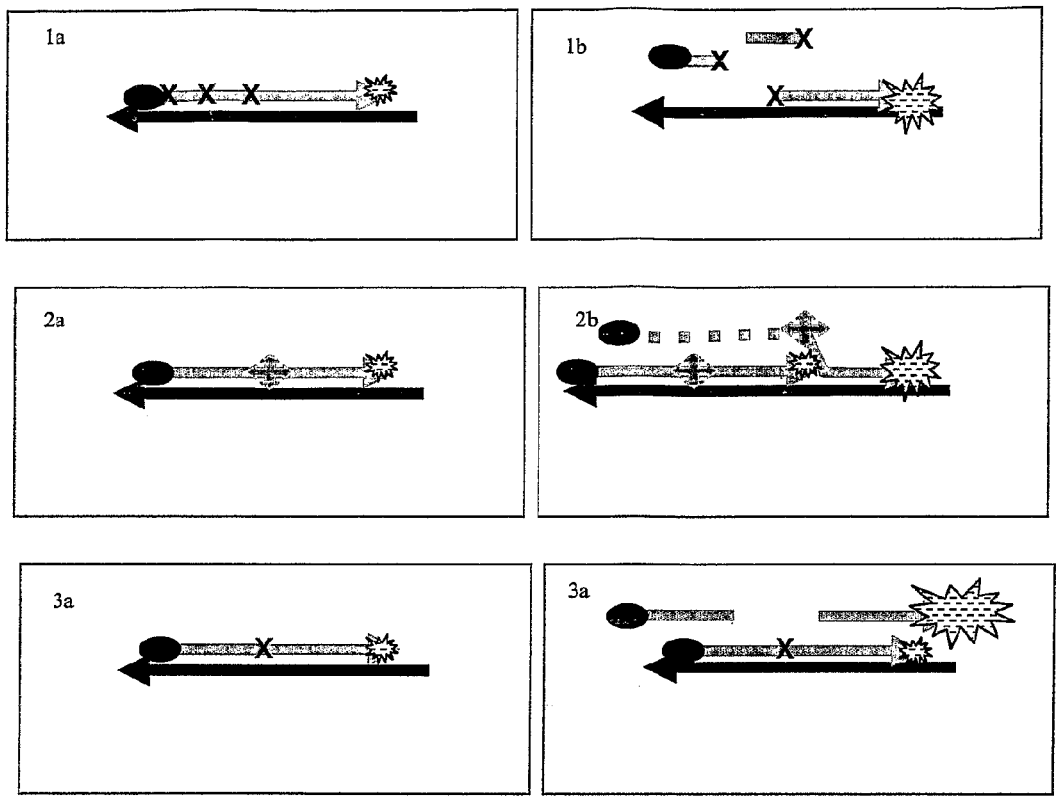
FIG. 4 illustrates different primer and probe designs.

FIG. 4 illustrates various primer and probe designs.

The figures illustrate various primer and probe designs. In particular, the figures relate to systems that utilise a quencher (black solid circle) and a fluorophore (hatched star). Where fluorescence is quenched the star is shown to be reduced in size compared with that exhibiting full fluorescence. However, the methods of primer/probe cleavage illustrated apply equally to non-labelled primers.

1a: In this example a primer (grey) comprises several moieties marked as "X" which are cleaved by an endonuclease after the primer binds to its complementary template. Examples of such moieties are 8-oxoguanine or unstable abasic residues that are cleaved by oxoguanine glycosylase in a duplex dependent manner. Such moieties are preferentially placed such that they are opposite a cytosine when the primer binds to the template (black). Where a glycosylase is used for primer destruction then elements must be placed within the primer that are cognate for the glycosylase. Such elements are preferentially placed three to five bases apart such that the activity of a glycosylase is minimally effected with respect to the substrate and also such that the cleaved fragments have a low affinity for the template and consequently minimally interfere with the binding of the replacement primer.

1b: When the primer (grey) binds to the template (black) an endonuclease recognises the lesions (X) and cleaves the backbone of the nucleic acid primer. The primer is designed such that the uncleaved 3' terminus remains bound to the template due to its melting temperature which is higher than that of the fragmented 5' terminus. The melting temperature of the fragments is such that they are lower than the ambient temperature of the reaction. The melting temperature of the 3' terminus may be intrinsically higher than the fragments or it may be higher due to its extension by the polymerase during the reaction. The area of template exposed by cleavage of the primer must be large enough such that a further intact primer is able to bind to this region. It is also important that the fragments are not extendable or are not extended prior to their release. In the case of oxoguanine dependent cleavage, the fragments produced are essentially inert.

2a-2b: In this example the essential features of the primer are similar to those of 1a-1b. In this case a duplex dependent 5'-3' exonuclease is used instead of an endonuclease. The primer has bases modified in its mid-section that are resistant to the cleavage by the exonuclease. Typically where these bases are phosphorothioate linkages between bases then one to four phosphorothioate moieties induce complete resistance to exonuclease digestion. As such the 5' nucleotides are removed without cleavage of the primer 3' terminus.

3a: This example shows a primer designed to generate a detectable signal during amplification. In this example the primer (grey) has a fluorescent quencher (black circle) and a fluorophore (hatched star) placed at moieties such that one element is within the fragmentable region and the other in present within the 3' region of the primer. The fluorophore is therefore quenched when the primer is intact.

3b: During cleavage as shown in boxes 1 and 2 one or both of the fluorophore or quencher moieties are released, thus separating the fluorophore from the quencher which increases the fluorescence. This system may be implemented within an amplifiable primer or may have a non extendable 3' terminus and form part of a probe which is used purely to detect a sequence being amplified.

Destruction of Primer

The destruction of the 5' terminus of the primer may be achieved by numerous means but must have the following properties. It must be primarily dependent on the primer being bound to its cognate element of the template and in this sense it must primarily depend on the primer being part of a duplex nucleic acid and also allow the features described for primer design.

The fragments produced by digestion of the primer must be essentially non-extendible. Clearly the 3' residual primer should be extended or extendable.

The 5' fragments should not interfere significantly with the binding of further primers to the exposed (single stranded) region of the template.

The cleavage of the primer must include as a primary or secondary reaction of the cleavage enzyme, the cleavage of the backbone of the primer.

The cleavage must only include the primer without cleavage of the backbone of the template.

It is also essential that the elements within the primer can be copied onto by the polymerase used within the amplification system.

The cleavage of the primer may be achieved by 5'-3' duplex dependent exonucleases or by nucleic acid repair enzymes such as DNA glycosylases or DNA Apurinic endonucleases or the cleavage may be achieved by chemical means (Biochem. Biophys. Res. Commun. 1991 Dec. 31; 181(3):1266-72).

In one embodiment the primer 5' terminus is destroyed by a glycosylase. Numerous glycosylases are useful for this purpose but the primer must comprise bases cognate for the particular glycosylase.

Typically the glycosylase may be one from a list of oxoguanine glycosylase, Fpg (formamidopyrimidine [fapy]-DNA glycosylase) endonuclease III endonuclease IV endonuclease VIII or human oxoguanine glycosylase hOGG1 or their thermophilic equivalents.

Numerous cognate bases that are substrates for the said endonuclease/glycosylase may be incorporated into the synthetic oligonucleotide primer including 7,8-dihydro-8-oxoguanine (8-oxoguanine), 8-oxoadenine, fapy-guanine, methyl-fapy-guanine, fapy-adenine, aflatoxin B1-fapy-guanine, 5-hydroxy-cytosine and 5-hydroxy-uracil.

Duplex specific abasic endonucleases may also be used where these are in concert with an abasic site introduced into the nucleic acid primer. This can be achieved during synthesis where the enzyme is sensitive to stable abasic elements or due to the product of a Uracil placed into the primer where it is impacted by a Uracil glycosylase which leaves an unstable abasic residue.

Several of the abasic endonucleases as well as glycosylases do not have significant duplex dependence. It is found that the duplex specificity can be improved by altering buffer conditions. Inclusion of the pyrophosphate analogue (orthovanadate) to 8 mM or increasing the ionic strength of the solution to above 70 mM NaCl improves duplex specificity to the necessary extent.

Where 8-oxoguanine glycosylase (OGG1) is used then its preferred substrate is 8-oxoguanine and the lesion should be placed opposite to a cytosine. The thermostable oxo-guanine glycosylases exemplified by OGG from *Archaeoglobus fulgidus* (Mutation Research 486 (2001) 99-111) may also be used and these have the desired duplex specificity but do not require a cognate cytosine. It is also advantageous to add bromoguanine to the mixture in order to facilitate oxoguanine glycosylase digestion. Typically 50 uM bromoguanine is found to be effective.

A 5'-3' exonuclease may also be used. This activity is occupied by a broad range of enzymes. Again these must have the desired duplex specificity however the fragments produced are rendered inert in the system due to their small size. In the preferred embodiment the enzyme is T7-exonuclease (T7-gene-6). Other enzymes capable of this activity are lambda exonuclease and several exonuclease domains of thermophilic and mesophilic polymerases. In general where the domain of the exonuclease is part of an intact polymerase then the domain also has the requirement for an upstream duplex. This feature is not compatible with the preferred configuration of the invention. In contrast it is found that the cleaved 5'-3' exonuclease domain of such enzymes lose their requirement for upstream duplexes. Additional enzymes with significant 5'-3' exonuclease activity include the flap-endonucleases.

It is important that the 3' terminus of the primer or its extended product are protected from cleavage. This may be achieved by placing an exonuclease resistant moiety separating the 3' terminus from the 5' terminus of the primer or it may be achieved by balancing the enzymatic constituents of the system in such a way that the primer is on partially cleaved before it is invaded and displaced by an additional primer. Typically where moieties resistant to exonuclease digestion are used then these may comprise phosphorothioate linkages between bases. One to four phosphorothioate moieties generally induce complete resistance to exonuclease digestion (Nikiforov T T et al PCR Methods Appl. 3(5):285-91).

Yet another embodiment of the invention relies on RNA/DNA chimeric primers. The RNA elements are placed in the destructible area of the primer and typically these are removed by enzymes in the RNAse-H family which have specificity for RNA-DNA duplexes. Where RNA-DNA chimeras are used then it important that a polymerase with reverse transcriptase activity is utilised as part of the system since one of the essential features of the system is that the complete primer must be copied by the polymerase.

In theory it is plausible the 5' terminus of the primer is left intact and that the middle portion of the primer is destroyed such that a new primer binds to this portion of exposed template which, as described enables invasion of the original primer elements bound at both the 3' and 5' terminus. This is essentially the same phenomenon described within the invention since the 5' terminus of the primer becomes essentially inert.

Several abasic endonucleases cleave the backbone of a primer at an abasic site which has been introduced during synthesis or by the action of a glycosylase. Some of these enzymes induce fragments with an extendable 3' terminus. In order to negate this extension it is possible to reduce the distance between abasic elements such that the melting temperature of the fragments produced ensures that the fragment is rapidly released.

Enhancement of Strand Invasion

Strand invasion is an essential aspect of the system in that the replacement primer binds to the area of the extended primer template complex at the 3' terminus of the template which represents the 5' terminus of the replacement primer. The 3' terminus of the replacement primer must invade the 5' terminus of the original extended primer and displace it as the new primer is extended by the polymerase.

It is advantageous that the replacement primer invades and extends prior to its cleavage by the system used to degrade its 5' terminus. This is important since, if the degradation preceded invasion then the 3' terminus of the primer will be not be anchored proximal to the template and since it will consequently be removed, invasion and extension will not take place.

Several methods are available to enhance strand invasion. In the preferred embodiment this is achieved by the application of proline which is found to enhance this process. A similar effect is also found with other osmoprotectants including betaine. Other moieties that may enhance this effect are alterations magnesium ion concentration as well as the application of detergents. The precise mechanism whereby these components facilitate invasion is not known but they have been reported to decrease the stability of duple nucleic acids (FEBS Letters 410 (1997) 201-205) containing cytosine-guanine bonds and it is presumed that this facilitates strand exchange. It should be understood that any mechanism facilitating strand invasion or exchange may by used but are not found to be essential since the system is viable without addition of these enhancers.

Enhancement of strand invasion may also be achieved by extending the length of the degradable aspect of the primer. The primer intrinsically forms a more stable complex with the template and as such it can be degraded to a greater extent before template binding is significantly reduced. This allows more time and presents a more stable primer template complex facilitating the invasion event.

An additional method of enhancing the balance of the system in favour of strand invasion is alteration in the concentration of enzyme constituents such that the rate of primer cleavage is reduced to the extent that strand invasion is favoured in the system.

Signal Detection

The product of amplification may be detected for qualitative or quantitative purposes by numerous methods. Signal generation methods may be an intrinsic aspect of the amplification process and utilise aspects of the invention or they may utilise the product as part of an additional process removed from the subject herein.

Numerous methods of signal detection require the utilisation of single stranded nucleic acid. The invention allows for this by a number of mechanisms.

Single stranded products may be induced by altering the concentration of a particular primer or probe within the system. Where one of the primers is supplied to the system at a higher concentration than other primer elements then one side of the reaction, being either the production of the forward product or the reverse product will be favoured. By way of an example where the reverse primer part of the system is at a higher concentration than the forward aspect then after the forward primer is fully incorporated into the product then excess reverse primer remains available for continued reverse product production. Since no further forward product is produced the additional reverse product will not have a cognate template to bind and will remain single stranded. It is notable that where one side of the reaction is consumed then the reaction becomes linear rather than exponential. This linear amplification could be used as a variant of the amplification schema.

Single stranded product may also be produced by the application of a cleavable element within the non-destructed aspect of a primer and where the cleavable element is not the substrate for the enzyme system used within the amplification. Addition of the enzyme system cognate to the cleavable lesion after completion of the reaction may be used to induce the complete destruction of a primer product.

By way of example the current invention allows for primer destruction by exonuclease or glycosylases. Generally the exonuclease cleaves the 5' terminal nucleosides to a point that is protected by a resistant residue. This process may be used for amplification but it is possible to place a glycosylase cognate residue within the non destructed portion of one of two primers (forward or reverse) such that after amplification is completed the protected area of a product is cleaved by the addition of the said glycosylase wherein the cleaved extended primer product becomes a substrate for the exonuclease resulting in the complete destruction of either the forward or reverse complement of the product and retaining only a single strand.

A probe may be utilised for signal detection that incorporates aspects of the amplification schema. A probe is used to detect the presence or absence of a specific sequence which is amplified. A probe may generate a signal as a direct consequence of binding to its cognate element or it may be a capture probe may be used such that upon binding to its amplified cognate element it can be separated from the remaining components and then such elements are detected subsequently.

Within the present invention a probe may be extendible by its 3' terminus or non-extendable. Any probe must be partly or completely cognate to an amplified sequence that it is designed to detect.

Typically a probe will comprise a signal generating element and an element that alters the said signal by way of the proximity between the two elements. By way of example a fluorescent quencher based system relies on the proximity between fluorophore and quencher. In these systems the quencher may be removed and the fluorescent signal increases. The proximity of the moieties may be altered as a direct consequence of binding as exemplified by a molecular beacon or due to cleavage of the probe. Where a molecular beacon configuration is utilised then the 5' terminus of the probe can be protected from cleavage either by ensuring that it is not cognate to the template or by the lack of lesions in the probe or by protecting its 5' terminus with an exonuclease resistant moiety.

Where signal is generated by cleavage of the probe then the one moiety of the quenched or FRET pair may be within the destructible aspect of the primer and the other within the non destructible element. Destruction of the probe may utilise the same destructible system as that used within the amplification or an alternative destructible system as mentioned herein. By way of example, the probe may comprise an 8-oxoguanine as the cleavable element such that it is cleaved by hOGG1. It is advantageous that cleavage of the probe results in probe fragments that have a lower affinity for the amplicon such that a further probe will bind and become cleaved enhancing the generation of signal. Where an exonuclease is utilised then it is differentiated from the probe described in U.S. Pat. Nos. 5,487,972, 5,538,848 and 5,723,5915 since within these patents the exonuclease is a quality of the polymerase used for amplification rather than added to the system. Furthermore the probes used within adaptor based systems are preferably of a hairpin structure.

The method for generating detectible signal may involve a change in frank fluorescence (FF), fluorescence resonance energy transfer (FRET), fluorescence quenching (FQu), time resolved fluorescence (TRF), a radioactive label proximity assay (RLPA), or Raman scatter (RS), surface enhanced Raman scatter (SERS), fluorescent lifetimes (FLIM), fluorescence correlation (FCS), fluorescence intensity distribution analysis (FIDA), fluorescence polarization (FP), bioluminescence resonance energy transfer (BRET), chemiluminescence resonance energy transfer (CRET), surface Plasmon resonance (SPR) or total internal reflectance (TIR) fluorescence.

It is a fundamental consideration of the invention that a probe or a primer will not generate a signal if it is not cognate to the template being amplified. This is also found to be true if the moieties are only partially cognate under some conditions. Specifically if the 3' terminus of an adaptor is not cognate to a template it will not extend efficiently by the action of a polymerase during the initial stage of amplification. Equally if the bases on the primer that are the substrate for a duplex specific enzyme used to destroy the 5' terminus of the primer are not cognate then amplification will also be initially inhibited. If the probe is altered in a similar fashion then the consequent signal produced is reduced.

Due to the considerations above, the system can be used to detect the presence or absence of a single base or a change in the nature of a single base in a template sequence. In this respect the system can be used to detect single nucleotide polymorphisms (SNPs).

In the preferred embodiment of the invention the detection system comprises a nucleic acid that is extendible from its 3' terminus (the adaptor sequence) and a second nucleic acid that is not extendable (the probe).

This probe comprises a fluorophore and a quencher in close proximity which are intervened by or overlapped by an element that causes destruction of the probe when it is in a double stranded complex. Such sequences are exemplified by 8-oxoguanine in the presence of hOGG1 or any sequence in the presence of T7 exonuclease.

The adaptor comprises a region proximal to its 3' terminus that is cognate to the amplicon. Therefore this cognate sequence represents and is cognate to at least part of the sequence that is amplified between the forward and the reverse primer. Upstream of (5' to) this amplicon binding sequence there may be an additional nucleic acid sequence that forms a nicking endonuclease recognition sequence. Upstream of the restriction endonuclease recognition sequence is a sequence that is similar to the probe sequence or part of the probe sequence. The nicking endonuclease sequence is configured such that if the adaptor forms part of a duplex then the strand complementary to the adaptor is nicked. It is possible to use an endonuclease that induces cleavage of both strands but where the recognition sequence within the adaptor is protected from cleavage by the introduction of a phosphorothioate molecule at its cleavage site. In this case only the opposite strand is cleaved.

An example of restriction endonucleases that are compatible with this system are Nt.BbvC (New England Biolabs) and EcoRI. Typically 10-100 units of Nt.BbVC or EcoRI may be utilised for 50 ul of a reaction mixture comprising 200 nM of adaptor. In the case of NtBbvc the adaptor comprises the sequence 5'GCTGAGG. An extendible nick is consequently induced in the complementary strand at the position CGACT/CC where "/" represents a cleavage site. In the case of EcoRI the sequence G*AATTC is included in the adaptor where "*" represents a phosphorothioate linkage. Although EcoRI induces cleavage of both nucleic acid strands the phosphorothioate protects the adaptor strand from being cleaved.

Where the amplification described within the invention would induce destruction of the adaptor such as those systems that rely on T7-exonuclease digestion of primers then the adaptor is protected from digestion by including a series of phosphorothioate molecules at its very 5' terminus.

During the amplification process the adaptor is therefore able to bind to the released single stranded amplicon. The adaptor extends and therefore copies a sequence that is complementary to a primer (the downstream primer) used in the amplification process.

The adaptor is displaced by the upstream primer since the upstream primer binds to the same single stranded amplicon.

The displaced adaptor is then able to bind to the downstream primer and the downstream primer extends onto the adaptor.

Once the downstream primer has extended onto the adaptor the nicking recognition site becomes double stranded and is therefore competent for binding to and cleavage by the endonuclease.

The complementary adaptor strand which is the extended downstream primer is therefore cleaved. The cleaved adaptor complement then extends displacing the complement of the probe sequence.

The cleavage process is repeated re-iteratively releasing a supply of a sequence complementary to the probe.

The probe is able to bind to this sequence and is cleaved which increase the fluorescence in the test system.

The probe may form a hairpin structure and a three prime sequence additional to and outside the hairpin such that the fragment displaced from the adaptor binds to the three prime sequence of the probe extending into the hairpin structure of the probe. The fluorescence of the system may be increased by opening of the hairpin structure due to extension of the nicked fragment that is bound to the probe such that the proximity of the fluorophore and quencher is increased. Alternatively the probe may comprise the cleavable elements described herein and destruction of the probe increases the fluorescence of the system by release of fluorophore from quencher.

Strand Displacement

The polymerases used in the process of the invention are preferably those with strand displacement activity. This activity is a well-known property of certain DNA polymerases (Sambrook et al., 1989, Molecular Cloning: A Laboratory Manual, 2nd edition, pp. 5.33-5.35, Cold Spring Harbor Laboratory, Cold Spring Harbor). The properties of the DNA polymerases, particularly the strand displacement activity of some of them, are given in detail by Kornberg and Baker, DNA Replication, 2nd edition, pp. 113-225, Freeman, N.Y. (1992). Strand displacement is not a property common to all DNA polymerases since some of them, like T4 DNA polymerases, are not capable of accomplishing strand displacement alone. Strand displacement activity was shown initially for the Klenow fragment of *Escherichia coli* DNA polymerase I (Masamune and Richardson, 1971, J. Biol. Chem. 246: 2692-2701), which confers on this enzyme the capability of initiating replication of nucleic acid from the 3'OH end of a cleavage site in a double-stranded DNA. This strand displacement activity has also been shown in thermostable DNA polymerases such as Tli DNA polymerase (Kong et al., 1993. J. Biol. Chem. 268: 1965-1975). In this case it has also been shown that mutated forms of this enzyme do not have exonuclease 5'-3' activity that has a higher strand displacement capacity. This strand displacement activity has also been shown for T7 DNA polymerase (Lechner et al., 1983. J. Biol.

Chem. 258: 11174-11184) and for HIV reverse transcriptase (Huber et al., 1989, J. Biol. Chem. 264: 4669-4678).

Preferably, a DNA polymerase with no 5'-3' exonuclease activity is used to accomplish the amplification cycle according to the invention since the effectiveness of the strand displacement activity is greater in enzymes with no such exonuclease activity. The Klenow fragment of *Escherichia coli* DNA polymerase I is an example of a polymerase with no 5'-3' exonuclease activity, as are polymerases such as T7 DNA polymerase or Sequenase (US Biochemical). T5 DNA polymerase or Phi29 DNA polymerase can also be used. However, a DNA polymerase having this 5'-3' exonuclease activity can be used when it does not prevent the amplification process from being carried out. In this case, the yield of the amplification reaction can be improved by specific inhibition of the 5'-3' exonuclease activity of DNA polymerases under the reaction conditions employed.

The present amplification process requires a reverse transcription step when the starting product is an RNA. This conversion step, of RNA into cDNA can also be accomplished by using reverse transcriptase such as AMV (avian myeloblastosis virus) or MMLV (Moloney murine leukemia virus), both available commercially. Any other enzyme with RNA- or DNA-dependent DNA polymerase activity can be used in the present invention provided it has strand displacement activity. In the contrary case, the strand displacement activity can be conferred by an inducer agent, activity of the helicase type, or Rec A. The properties of Rec A, particularly in the process of single-stranded DNA reassociation, strand capture, or strand assimilation are described in detail by McEntee and Weinstock in "The Enzymes," vol. XIV, pp. 445-470. The reverse transcription step can for example be accomplished with *Escherichia coli* DNA polymerase I as it has been shown that this enzyme also has RNA-dependent DNA polymerase activity (Ricchetti and Buc, 1993. EMBO 12: 387-396). For this purpose, RNA- and/or DNA-dependent thermostable DNA polymerases such as Taq polymerase or Tth polymerase can also be used; for a survey of the properties of thermostable DNA polymerases, see Rolf et al., PCR: Clinical Diagnostics and Research, pp. 224-258, Springer-Verlag, Heidelberg (1992).

Stand displacement may also be enhanced by the application of enzyme systems or other elements that stabilise single stranded rather than duplex DNA. Examples of such systems are the application of DNA helicases, stabilisation by single stranded binding proteins as well as the influence of the particular polymerase used in the system. It is essential that the method of enhancement of strand displacement does not interfere with the processes of strand invasion. Since the majority of single stranded binding proteins stabilise the 3' terminus of a new primer before it has invaded the product, it is preferred that the method for enhancement of strand displacement involves strand displacing polymerases alone or in concert with a helicase system.

Where RNAseH is added to the system or where a 5' exonuclease is either added or an aspect of the polymerase used for amplification then a RNA polymerase that has primase activity can be used to temporarily add bases complementary to the displaced template. These bases are removed by the action of the said enzymes during the amplification process. The temporary addition of these bases also helps to stabilise the displaced strand and facilitate amplification. Clearly this method of amplification enhancement may be applied to any isothermal amplification technique.

EXAMPLES

Example 1

Figure 5:
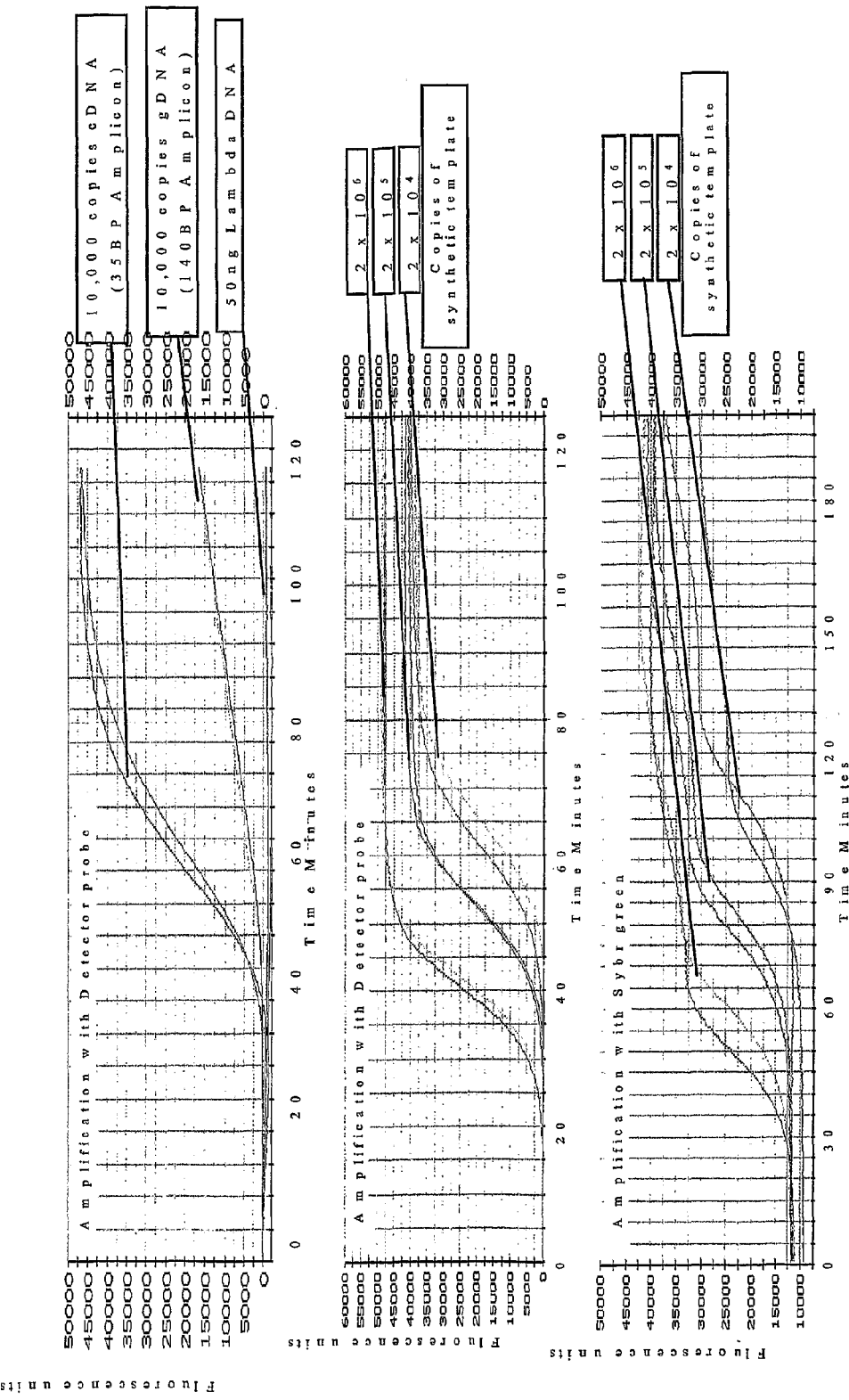
FIG. 5 shows exonuclease-dependent amplification detected by a fluorescence probe or Sybr Green (Example 1).

See FIG. 5

Exonuclease Dependent Isothermal Amplification Using a Fluorescent Detector Probe All reagents used were molecular biology grade and obtained from Sigma-Aldrich. T7 gene 6 exonuclease (50 U/µl) was purchased from GE Healthcare, Klenow Fragment 3'-5' exo⁻ (10 U/µl) and high purity standard deoxynucleoside triphosphates (dNTPs) were purchased from Jena Bioscience, Loebstedter Str 78, Jena, Germany. Oligonucleotide primers and synthetic template were purchased from Thermo Electron and were HPLC purified. PCR-ready Human hepatic cDNA (0.5 ng/µl) was purchased from Ambion Inc, Austin Tex., Human genomic DNA (buffy coat) (200 ng/µl) was purchased from Roche and Lambda phage DNA (500 ng/µl) was purchased from NEB. Sybr Green I was purchased from Invitrogen.

The sequence of oligonucleotide primers, detector probe and template sequences used in this example are given in table 1.

TABLE 1

| | | |
|---|---|---|
| PTO-P2 | 5' CT<u>CAACGACCA</u>*C*T*T*TGTCAAG | [SEQ. ID NO: 1] |
| PTO-P1 | 5' <u>TAGCCAAATTC</u>*G*T*T*GTCATA | [SEQ. ID NO: 2] |
| Detector Probe comprising 5' fluorescein and 3' black hole quencher which renders the probe non extendible | 5' AGCTCATTTCCTGGTA | [SEQ. ID NO: 22] |
| Synthetic oligonucleotide template | 5' <u>CAACGACCACTTTGTCAAG</u>CTCATTTCCTGG<u>TATGACAACGAATTTGGCTA</u> CAGCA | [SEQ. ID NO: 3] |
| Partial cDNA sequence | 5' . . . CT<u>CAACGACCACTTTGTCAAG</u>CTCATTTCCTGG<u>TATGACAACGAA TTTGGCTA</u> . . . | [SEQ. ID NO: 4] |
| GAPDH genomic sequence | . . . CT<u>CAACGACCACTTTGTCAAG</u>CTCATTTCCTGGTATGTGGCTGGGCC AGAGACTGGCTCTTAAAAAGTGCAGGGTCTGGCGCCCTCTGGTGGCTGGCTCAG AAAAAGGGCCCTGACAACTCTTTTCATCTTCTAGG<u>TATGACAACGAATTTGGCT</u> <u>A</u>CAG . . . | [SEQ. ID NO: 5] |

*denotes phosphorothioate

Assay Components

All concentrations are the final concentrations in a reaction volume of 30 μl. Amplification primers PTO-P1 (0.5 μM) and PTO-P2 (0.25 μM) were used in combination with 0.2 μM detector probe or 1/30,000 Sybr green. The reaction components include an excess of dNTPs (200 μM of each nucleoside), 50 mM potassium acetate, 20 mM Tris-acetate (pH 7.9), 10 mM magnesium acetate, 5 mM dithiothreitol, 0.1 mg/ml bovine serum albumin, 2 M L-proline, 0.0625 units/μl T7 gene 6 exonuclease and 0.025 units/μl klenow fragment exo$^-$. Templates for amplification used including $10^4$ copies (50 ng) of human genomic DNA or $1 \times 10^4$ copies of human GAPDH cDNA in a complex mixture or a titration of synthetic oligonucleotide template from $2 \times 10^6$ to $2 \times 10^4$. In addition a negative control containing 50 ng of lambda genomic DNA was used.

Amplification Assay

The assay was performed using thin wall, 200 μl 96 well polypropylene PCR plate and a Bio-Rad I-cycler to detect real-time fluorescence changes. All the assay components excluding the enzymes were added to the plate to a final volume of 27 μl. The incubation of the reaction at 37° C. was preceded by an initial 4 minute incubation step at 95° C. The reaction was initiated at 37° C. by addition of 3 μl of a 10× stock enzyme mixture containing 0.625 units/μl T7 gene 6 exonuclease and 0.25 units/μl Klenow fragment exo–. Real time fluorescence changes were recorded immediately after the addition of the enzyme mixture.

As shown in FIG. 5, the amplification process can be detected where the vertical axis presents the degree of fluorescence and the horizontal axis represents time. The fluorescence tends to increase with time where template under investigation is present but does not increase when the template DNA is not cognate to the primers or probe used in the system. In the top figure human genomic DNA, human cDNA and lambda phage DNA is used. Only human DNA contains the sequence under investigation (GAPDH). Lamda DNA does not contain the gene sequence. As shown in the materials section, genomic DNA comprise the primer regions used and these flank a central (amplicon) region of more than 100 base pairs. cDNA also comprises the relevant primer regions but these flank a much shorter sequence. As shown in the figure cDNA is amplified most efficiently due to its short amplicon region requiring less time to be displaced by the polymerase. Genomic DNA is amplified more slowly whereas Lambda DNA, which does not contain this sequence, is not amplified.

The two lower figures show the amplification of a synthetically manufactured single stranded sequence of DNA at differing concentrations and detected by other a sequence specific probe (middle figure) or the dye Sybr Green that detects duplex (amplified) DNA (lower figure). The time taken to amplify the sequence is proportional to the amount of starting material.

Example 2

Figure 6:
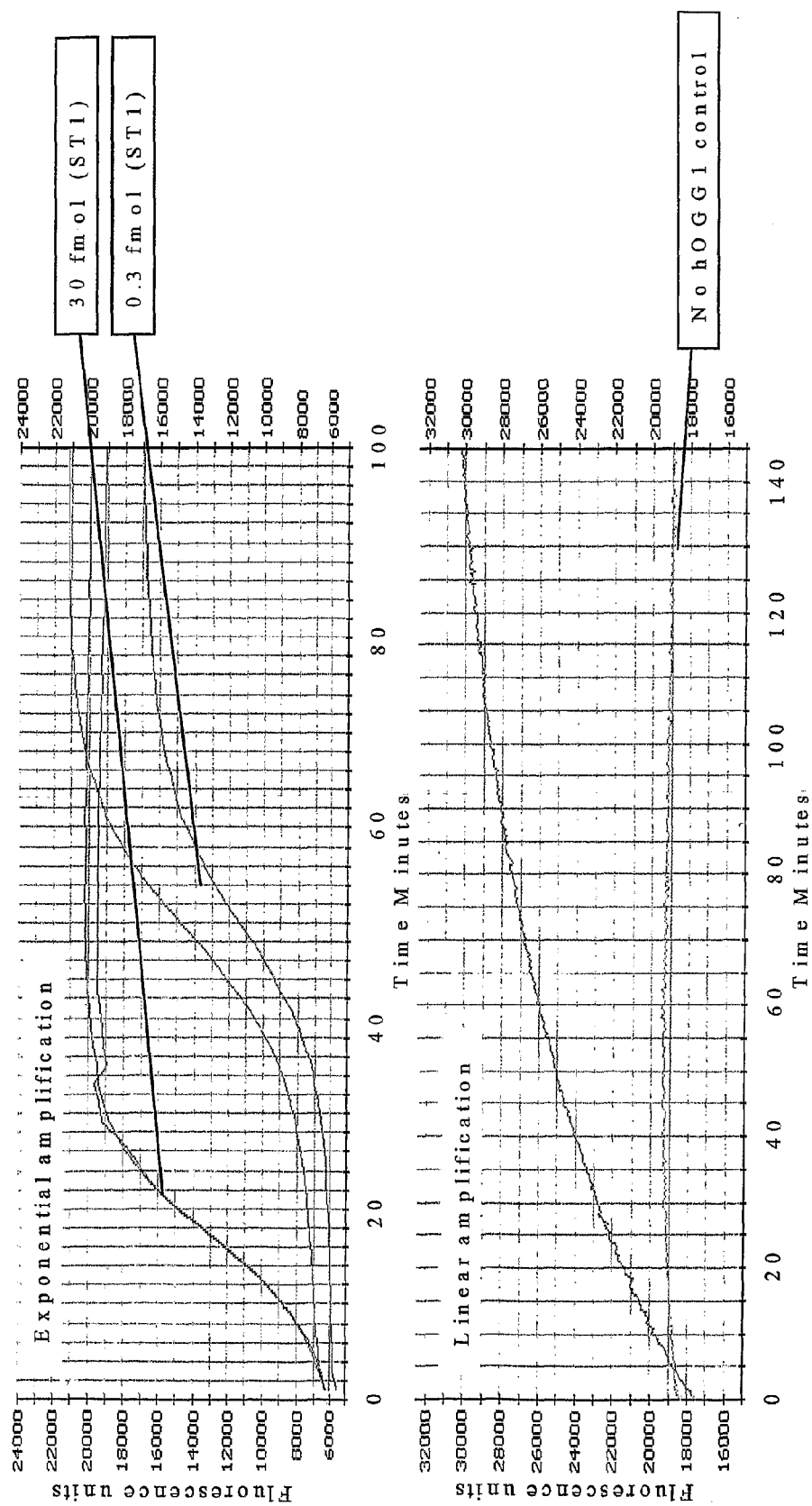
FIG. 6 shows endonuclease-dependent amplification detected with Sybr Green (Example 2).

See FIG. 6

Glycosylase Dependent Isothermal Amplification.

All reagents used were molecular biology grade and except where stated, were obtained from Sigma-Aldrich. Human 8-oxoguanine DNA glycosylase a isoform (hOGG1) (1.6 U/μl) was purchased from NEB, Klenow Fragment 3'-5' exo$^-$ (10 U/μl) Jena Bioscience, Loebstedter Str 78, Jena, Germany. Oligonucleotide primers and synthetic template were purchased from Thermo Electron and were HPLC purified. Sybr Green I was purchased from Invitrogen.

The sequence of oligonucleotide primers, detector probe and template sequences used in this example are given in table 2.

TABLE 2

| OX-P1 | 5' AGCATAGoCAAACoGATAAGTGGTCTAC | [SEQ. ID NO: 6] |
|---|---|---|
| OX-P2 | 5' CTTGAoTGCGTCAoTTGCTATGATCCAG | [SEQ. ID NO: 7] |
| Synthetic oligonucleotide template (ST1) | 5' CTTGAGTGCGTCAGTTGCTATGATCCAGCTGTAGACCACTTATC CGTTTGCCTATGCT | [SEQ. ID NO: 8] |

'o', 8-oxoguanmne

Assay Components

All concentrations are the final concentrations in a reaction volume of 50 μl.

Amplification primers OX-P1 and OX-P2 for exponential amplification were used at 0.5 μM or OX-P1 at 0.5 μM for linear amplification. The reaction components include an excess of dNTPs (125 μM dTTP and dGTP, 100 μM dATP and 1000 μM dCTP), 10 mM sodium chloride, 2 mM Tris-HCl pH 7.9, 2 mM magnesium chloride, 0.2 mM dithiothreitol, 50 μM bromoguanine, 0.05 mg/ml bovine serum albumin, 0.75 M L-proline, 1/30,000 Sybr green, 0.016 units/μl hOGG1 and 0.1 units/μl klenow fragment exo$^-$. ST1 (template) was used at mM and 10 μM for exponential amplification or at 20 nM for linear amplification. An additional control sample containing no hOGG1 was used for the linear amplification.

Amplification Assay

The assay was performed using thin wall, 200 μl, 96 well polypropylene PCR plate and a Bio-Rad I-cycler to detect real-time fluorescence changes. All the assay components excluding the enzymes were added to the plate to a final volume of 40 μl. The incubation of the reaction at 37° C. was preceded by an initial 4 minute incubation step at 95° C. The reaction was initiated at 37° C. by addition of 10 μl of a 5× stock enzyme mixture containing 0.08 units/μl hOGG1 and 0.5 units/μl Klenow fragment exo–. Real time fluorescence changes were recorded immediately after the addition of the enzyme mixture.

As shown in the top figure, time taken to detect amplification with Sybr Green is proportional to the amount of starting material (detailed above). The lower figure demonstrates result achieved with only one primer and detected with Sybr Green. In this example the amplification is linear instead of exponential until the primer concentration becomes rate limiting. Where the enzyme used to destroy the 5' region of the primer (hOGG1) is absent then no amplification is detected.

Example 3

RNase Dependent Isothermal Amplification Using a Fluorescent Detector Probe

All reagents are molecular biology grade and can be obtained from Sigma-Aldrich. *E. coli* RNase H (10 U/μl) can be purchased from Epicentre, Madison, Wis., Superscript II reverse transcriptase (200 U/μl) can be purchased from Invitrogen, RNase inhibitor (40 U/μl) can be purchased from Ambion Inc, Austin Tex., Klenow Fragment 3'-5' exo⁻ (10 U/μl) and high purity standard deoxynucleoside triphosphates (dNTPs) can be purchased from Jena Bioscience, Loebstedter Str 78, Jena, Germany. Oligonucleotide primers and synthetic template can be purchased from Thermo Electron and were HPLC purified. Sybr Green I is purchased from Invitrogen.

The sequence of oligonucleotide primers, detector probe and template sequences that can be used in this example are given in table 3.

by an initial 4 minute incubation step at 95° C. The reaction is initiated at 37° C. by addition of 3 μl of a 10× stock enzyme mixture containing 4 units/μl Superscript II reverse transcriptase, 0.025 units/μl Klenow fragment exo⁻; 0.16 units/μl RNase H. Real time fluorescence changes are recorded immediately after the addition of the enzyme mixture.

This example relies on RNA/DNA chimeric primers. The RNA elements are placed in the destructible area of the primers (RD-P1 and RD-P2). The RNA portion of the primer is destroyed upon binding and extension onto the sequence to be amplified by the action of RNAse-H which is also added to the system since this enzyme has specificity for RNA-DNA duplexes.

Primer RD-P1 can bind to the template (as shown by double underlined regions). After extension its 5' RNA region (shown in italics) is destroyed by RNase such that the primer can be replaced by a further similar primer. The displaced strand is then able to react with RD-P2 (as shown by a single underline). The displaced product of this reaction is again able to bind to RD-P1. In order for the system to amplify in an exponential fashion the product bound to primer RD-P1, must extend onto the primer. Since the 5' region of the primer comprises RNA, the system must utilise a reverse transcriptase that is also given to the system.

TABLE 3

| RD-P2 | 5' ctcaacgaccACTTTGTCAAG | [SEQ. ID NO: 9] |
|---|---|---|
| RD-P1 | 5' tagccaaattCGTTGTCATA | [SEQ. ID NO: 10] |
| Synthetic oligonucleotide template | 5' CAACGACCACTTTGTCAAGCTCATTTCCTGGTATGACAACGAATTTGGCTACAGCA | [SEQ. ID NO: 11] |

Lower case denotes ribonucleotides
50 mM Tris-HCl (pH 7.5), 100 mM NaCl, and 10 mM MgCl₂.

Assay Components

All concentrations are the final concentrations in a reaction volume of 30 μl. The reaction components include amplification primers RD-P1 (0.5 μM) and RD-P2 (0.5 μM), an excess of dNTPs (1 mM of each nucleoside), 50 mM Tris-HCl (pH 8.3), 40 mM potassium chloride, 6 mM magnesium chloride, 10 mM dithiothreitol, 0.1 mg/ml bovine serum albumin, 2 M L-proline, 1/30,000 Sybr green, 0.4 units/μl Superscript II reverse transcriptase, 0.025 units/μl Klenow fragment exo⁻, 0.016 units/μl RNase H, RNase inhibitor (1 U/μl).

Amplification Assay

The assay is performed using thin wall, 200 μl, 96 well polypropylene PCR plate and a Bio-Rad I-cycler to detect real-time fluorescence changes. All the assay components excluding the enzymes are added to the plate to a final volume of 27 μl. The incubation of the reaction at 37° C. is preceded Example 4

Exonuclease Dependent Isothermal Amplification Using an Adapter and a Glycosylase Cleavable Fluorescent Detector Probe (as Illustrated in FIG. 3)

All reagents used were molecular biology grade and obtained from Sigma-Aldrich. T7 gene 6 exonuclease (50 U/μl) was purchased from GE Healthcare, Human 8-oxoguanine DNA glycosylase α isoform (hOGG1) (1.6 U/μl) was purchased from NEB, Klenow Fragment 3'-5' exo⁻ (10 U/μl) and high purity standard deoxynucleoside triphosphates (dNTPs) were purchased from Jena Bioscience, Loebstedter Str 78, Jena, Germany. Oligonucleotide primers and synthetic template were purchased from Thermo Electron and were HPLC purified.

The sequence of oligonucleotide primers, detector probe, adapter and template sequences used in this example are given in table 4.

TABLE 4

| PTO-P2 | 5' CTCAACGACCA*C*T*T*TGTCAAG | [SEQ. ID NO: 12] |
|---|---|---|
| PTO-P1 | 5' TAGCCAAATTC*G*T*T*GTCATA | [SEQ. ID NO: 13] |
| Detector Probe comprising 5' fluorescein and 3' black hole quencher | 5' ACTTCAo CCAATCA | [SEQ. ID NO: 14] |
| Adapter | 5' T*T*C*A*G CCAATCAGTAGACCACTTA | [SEQ. ID NO: 15] |
| Synthetic oligonucleotide template | 5' CAACGACCACTTTGTCAAGGTAGACCACTTATATGACAACGAATTTGGC TACAGCA | [SEQ. ID NO: 16] |

*denotes phosphorotbioate,
'o' denotes 8-oxoguanine

Assay Components

All concentrations are the final concentrations in a reaction volume of 30 µl.

Amplification primers PTO-P1 (0.5 µM) and PTO-P2 (0.5 µM) were used in combination with 0.02 µM adapter and 0.2 µM detector probe. The reaction components include an excess of dNTPs (200 µM of each nucleoside), 50 mM potaspurity standard deoxynucleoside triphosphates (dNTPs) can be purchased from Jena Bioscience, Loebstedter Str 78, Jena, Germany. Oligonucleotide primers, probe and synthetic template can be purchased from Thermo Electron and are HPLC purified.

The sequence of oligonucleotide primers, probe and template sequences used in this example are given in table 5.

TABLE 5

| Probe | 5' AGGCACTCGATACCAATTA | [SEQ. ID NO: 17] |
|---|---|---|
| Amplification primer | 5' CTCAACGACCA*C*T*T*TGTCAAG | [SEQ. ID NO: 18] |
| Synthetic oligonucleotide template | 5' GCTGTAGCCAAATTcGAACTCATATAATTGGTATCGAGTGCCTTGACAAAGTGGTCGT TG | [SEQ. ID NO: 19] |
| Adapter | CAACGACCACTTTGTCAAGCGAACTCATATA | [SEQ. ID NO: 20] |
| Bumper primer | 5' GCTGTAGCCAAATT Bumper | [SEQ. ID NO: 21] | sium acetate, 20 mM Tris-acetate (pH 7.9), 10 mM magnesium acetate, 5 mM dithiothreitol, 0.1 mg/ml bovine serum albumin, 2 M L-proline, 0.0625 units/µl T7 gene 6 exonuclease 0.064 units/µl hOGG1, and 0.025 units/µl Klenow fragment exo⁻.

Amplification Assay

The assay was performed using thin wall, 200 µl, 96 well polypropylene PCR plate and a Bio-Rad I-cycler to detect real-time fluorescence changes. All the assay components excluding the enzymes were added to the plate to a final volume of 27 µl. The incubation of the reaction at 37° C. was preceded by an initial 4 minute incubation step at 95° C. The reaction was initiated at 37° C. by addition of 3 µl of a 10× stock enzyme mixture containing 0.625 units/µl T7 gene 6 exonuclease, 0.64 units/µl hOGG1 and 0.25 units/µl Klenow fragment exo-.

Example 5

Exonuclease Dependent Isothermal Amplification Using a Fluorescent Detector Probe and a Single Primer All reagents used are molecular biology grade and can be obtained from Sigma-Aldrich.

T7 gene 6 exonuclease (50 U/µl) can be purchased from GE Healthcare, Klenow Fragment 3'-5' exo⁻ (10 U/µl) and high Assay Components All concentrations are the final concentrations in a reaction volume of 30 µl.

Amplification primer (0.5 µM), bumper primer (0.01 µM) adapter (0.25 µM) were used in combination with 0.5 µM probe. The reaction components included an excess of dNTPs (200 µM of each nucleoside), 50 mM potassium acetate, 20 mM Tris-acetate (pH 7.9), 10 mM magnesium acetate, 5 mM dithiothreitol, 0.1 mg/ml bovine serum albumin, 2 M L-proline, 0.0625 units/µl T7 gene 6 exonuclease and 0.025 units/µl Klenow fragment exo⁻. A titration of synthetic oligonucleotide template from 2×10⁶ to 2×10⁴ was used to test amplification.

Amplification Assay

The assay is performed using thin wall, 200 µl, 96 well polypropylene PCR plate and a Bio-Rad I-cycler to detect real-time fluorescence changes. All the assay components excluding the enzymes are added to the plate to a final volume of 27 µl. The incubation of the reaction at 37° C. is preceded by an initial 4 minute incubation step at 95° C. The reaction is initiated at 37° C. by addition of 3 µl of a 10× stock enzyme mixture containing 0.625 units/µl T7 gene 6 exonuclease and 0.25 units/µl Klenow fragment exo-. Real time fluorescence changes are recorded immediately after the addition of the enzyme mixture.

As shown in FIG. 2, in this variation, the method is adapted to ultimately rely on a single primer, whereby the method is modified such that the reverse primer is replaced by the adaptor. The "amplification primer" binds to the template (double underline) and extends to produce a product which is able to bind to the adaptor. The adaptor comprises a region at its 3' terminus hybridised to the 3' end of product-1 and a region at its 5' terminus which has also similar to primer-1. Initially the adaptor 5' region is not cognate and the bumper primer binds to a region upstream of the hybridized adaptor subsequently removing it in order to facilitate the amplification process. As such, both ends of the template become adapted to bind to the amplification primer during subsequent steps as shown in FIG. 2.

The invention claimed is:

1. An isothermal process for amplifying a single stranded nucleic acid template which comprises:
    (a) applying a forward primer (primer-1) to the 3' region of the template;
    (b) extending said primer by a polymerase;
    (c) removing or degrading the 5' terminus of said primer to leave a partly degraded duplex product (product-1);
    (d) applying a further primer-1 molecule (primer-1a) to the region exposed by degradation of the 5' terminus of the extended primer (primer-1) so that the 5' region of said further primer (primer-1a) binds to the template;
    (e) allowing strand invasion of product-1 by the 3' terminus of said further primer (primer-1a), whereby the 3' terminus of said further primer hybridises with the template in place of the 5' terminus of product-1;
    (f) extending said primer-1a by a strand displacing polymerase causing release of product-1 (amplicon) from the template; and
    (g) reacting product-1 with a reverse primer (primer-2) which binds to the 3' region of product-1;
    (h) repeating steps (b) to (g) where the forward primer (primer-1) is replaced by the reverse primer (primer-2) in order to produce product-2 (amplicon);
wherein the original template is re-created by the reaction between product-2 and the 3' terminus of primer-1, whereby the 5' terminus of the primer is extended onto by the 3' terminus of the template.

2. The method of claim 1 wherein forward and/or reverse primers are adapted such that the 5' terminus can be removed or degraded whilst the 3' terminus cannot be removed or degraded.

3. The method of claim 1 wherein forward and/or reverse primers are adapted to bind to the template or product both via the 3' terminus alone and via the 5' terminus alone.

4. The method of claim 1 wherein removal or degradation of the primer is dependent on the primer being bound to the template DNA.

5. The method of claim 1 wherein the primer is cleaved by a 5'-3' duplex dependent exonuclease or an endonuclease.

6. The method of claim 5 wherein the 5'-3' duplex dependent exonuclease is T7 exonuclease or lambda exonuclease.

7. The method of claim 5 wherein the endonuclease is a nucleic acid repair enzyme.

8. The method of claim 7 wherein the nucleic acid repair enzyme is a DNA glycosylase or a DNA apurinic endonuclease.

9. The method of claim 8 wherein the DNA glycosylase is oxoguanine glycosylase, Fpg (formamidopyrimidine [fapy]-DNA glycosylase), endonuclease III, endonuclease IV, endonuclease VIII, or human oxoguanine glycosylase hOGG1, or their thermophilic equivalents.

10. The method of claim 1 wherein forward and/or reverse primers are cleaved by chemical means.

11. The method of claim 1 wherein the polymerase of step (b) has strand displacement activity.

12. The method of claim 1 wherein the polymerase of step (b) and/or step (f) has no 5'-3' exonuclease activity.

13. The method of claim 1 wherein the single stranded nucleic acid template consists of RNA and the method comprises an initial reverse transcription step before step (a).

14. The method of claim 1 wherein product-1 and/or product-2 (amplicon) is detected by a detectable probe which is cognate to the amplified sequence.

15. The method of claim 1 wherein the reverse primer (primer-2) comprises a region at its 3' terminus which is adapted to hybridize to the 3' end of product-1 and a region at its 5' terminus which has a complement which is adapted to hybridize to primer-1, whereby product-2 contains elements at its 5' terminus and at its 3' terminus that are adapted to react with primer-1 during steps (a) to (g) of the amplification process.

16. The method of claim 15 which further comprises applying a further primer (primer-3) to product-1 upstream of primer-2 thereby displacing product-2, primer-3 being adapted so as not to participate directly in the amplification process but to bind to product-1.

17. The method of claim 16 wherein primer-3 is adapted to be degraded when in duplex form.

* * * * *

```
                              SEQUENCE LISTING

<160> NUMBER OF SEQ ID NOS: 22

<210> SEQ ID NO 1
<211> LENGTH: 21
<212> TYPE: DNA
<213> ORGANISM: Artificial Sequence
<220> FEATURE:
<223> OTHER INFORMATION: primer with homology to human sequence
<220> FEATURE:
<221> NAME/KEY: misc_feature
<222> LOCATION: (11)..(14)
<223> OTHER INFORMATION: phosphorothioate

<400> SEQUENCE: 1
ctcaacgacc actttgtcaa g                                             21

<210> SEQ ID NO 2
<211> LENGTH: 20
<212> TYPE: DNA
<213> ORGANISM: Artificial Sequence
<220> FEATURE:
<223> OTHER INFORMATION: primer with homology to human sequence
<220> FEATURE:
<221> NAME/KEY: misc_feature
<222> LOCATION: (11)..(14)
<223> OTHER INFORMATION: phosphorothioate

<400> SEQUENCE: 2
tagccaaatt cgttgtcata                                               20

<210> SEQ ID NO 3
<211> LENGTH: 56
<212> TYPE: DNA
<213> ORGANISM: Artificial Sequence
<220> FEATURE:
<223> OTHER INFORMATION: template with homology to human sequence

<400> SEQUENCE: 3
caacgaccac tttgtcaagc tcatttcctg gtatgacaac gaatttggct acagca       56

<210> SEQ ID NO 4
<211> LENGTH: 53
<212> TYPE: DNA
<213> ORGANISM: Artificial Sequence
<220> FEATURE:
<223> OTHER INFORMATION: partial cDNA sequence

<400> SEQUENCE: 4
ctcaacgacc actttgtcaa gctcatttcc tggtatgaca acgaatttgg cta          53

<210> SEQ ID NO 5
<211> LENGTH: 160
<212> TYPE: DNA
<213> ORGANISM: Artificial Sequence
<220> FEATURE:
<223> OTHER INFORMATION: GAODH genomic sequence
```

-continued

```
<400> SEQUENCE: 5
ctcaacgacc actttgtcaa gctcatttcc tggtatgtgg ctggggccag agactggctc    60
ttaaaaagtg cagggtctgg cgccctctgg tggctggctc agaaaaaggg ccctgacaac   120
tcttttcatc ttctaggtat gacaacgaat ttggctacag                         160

<210> SEQ ID NO 6
<211> LENGTH: 28
<212> TYPE: DNA
<213> ORGANISM: Artificial Sequence
<220> FEATURE:
<223> OTHER INFORMATION: primer with homology to human sequence
<220> FEATURE:
<221> NAME/KEY: misc_feature
<222> LOCATION: (8)..(8)
<223> OTHER INFORMATION: n is 8-oxoguanine
<220> FEATURE:
<221> NAME/KEY: misc_feature
<222> LOCATION: (14)..(14)
<223> OTHER INFORMATION: n is 8-oxoguanine

<400> SEQUENCE: 6
agcatagnca aacngataag tggtctac                                       28

<210> SEQ ID NO 7
<211> LENGTH: 28
<212> TYPE: DNA
<213> ORGANISM: Artificial Sequence
<220> FEATURE:
<223> OTHER INFORMATION: primer with homology to human sequence
<220> FEATURE:
<221> NAME/KEY: misc_feature
<222> LOCATION: (6)..(6)
<223> OTHER INFORMATION: n is 8-oxoguanine
<220> FEATURE:
<221> NAME/KEY: misc_feature
<222> LOCATION: (14)..(14)
<223> OTHER INFORMATION: n is 8-oxoguanine

<400> SEQUENCE: 7
cttgantgcg tcanttgcta tgatccag                                       28

<210> SEQ ID NO 8
<211> LENGTH: 58
<212> TYPE: DNA
<213> ORGANISM: Artificial Sequence
<220> FEATURE:
<223> OTHER INFORMATION: synthetic template

<400> SEQUENCE: 8
cttgagtgcg tcagttgcta tgatccagct gtagaccact tatccgtttg cctatgct     58

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
ctcaacgacc actttgtcaa g                                              21

<210> SEQ ID NO 10
<211> LENGTH: 20
<212> TYPE: DNA
<213> ORGANISM: Artificial Sequence
<220> FEATURE:
<223> OTHER INFORMATION: primer
```

```
<400> SEQUENCE: 10
tagccaaatt cgttgtcata                                           20

<210> SEQ ID NO 11
<211> LENGTH: 56
<212> TYPE: DNA
<213> ORGANISM: Artificial Sequence
<220> FEATURE:
<223> OTHER INFORMATION: synthetic template

<400> SEQUENCE: 11
caacgaccac tttgtcaagc tcatttcctg gtatgacaac gaatttggct acagca    56

<210> SEQ ID NO 12
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (11)..(14)
<223> OTHER INFORMATION: phosphorothioate

<400> SEQUENCE: 12
ctcaacgacc actttgtcaa g                                         21

<210> SEQ ID NO 13
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (11)..(14)
<223> OTHER INFORMATION: phosphorothioate

<400> SEQUENCE: 13
tagccaaatt cgttgtcata                                           20

<210> SEQ ID NO 14
<211> LENGTH: 14
<212> TYPE: DNA
<213> ORGANISM: Artificial Sequence
<220> FEATURE:
<223> OTHER INFORMATION: detector probe
<220> FEATURE:
<221> NAME/KEY: misc_feature
<222> LOCATION: (7)..(7)
<223> OTHER INFORMATION: n is 8-oxoguanine

<400> SEQUENCE: 14
acttcancca atca                                                 14

<210> SEQ ID NO 15
<211> LENGTH: 24
<212> TYPE: DNA
<213> ORGANISM: Artificial Sequence
<220> FEATURE:
<223> OTHER INFORMATION: adaptor
<220> FEATURE:
<221> NAME/KEY: misc_feature
<222> LOCATION: (1)..(4)
<223> OTHER INFORMATION: phosphorothioate

<400> SEQUENCE: 15
ttcagccaat cagtagacca ctta                                      24
```

```
<210> SEQ ID NO 16
<211> LENGTH: 56
<212> TYPE: DNA
<213> ORGANISM: Artificial Sequence
<220> FEATURE:
<223> OTHER INFORMATION: synthetic template

<400> SEQUENCE: 16
caacgaccac tttgtcaagg tagaccactt atatgacaac gaatttggct acagca          56

<210> SEQ ID NO 17
<211> LENGTH: 19
<212> TYPE: DNA
<213> ORGANISM: Artificial Sequence
<220> FEATURE:
<223> OTHER INFORMATION: probe

<400> SEQUENCE: 17
aggcactcga taccaatta                                                   19

<210> SEQ ID NO 18
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (11)..(14)
<223> OTHER INFORMATION: phosphorothioate

<400> SEQUENCE: 18
ctcaacgacc actttgtcaa g                                                21

<210> SEQ ID NO 19
<211> LENGTH: 60
<212> TYPE: DNA
<213> ORGANISM: Artificial Sequence
<220> FEATURE:
<223> OTHER INFORMATION: synthetic template

<400> SEQUENCE: 19
gctgtagcca aattcgaact catataattg gtatcgagtg ccttgacaaa gtggtcgttg      60

<210> SEQ ID NO 20
<211> LENGTH: 31
<212> TYPE: DNA
<213> ORGANISM: Artificial Sequence
<220> FEATURE:
<223> OTHER INFORMATION: adaptor

<400> SEQUENCE: 20
caacgaccac tttgtcaagc gaactcatat a                                     31

<210> SEQ ID NO 21
<211> LENGTH: 14
<212> TYPE: DNA
<213> ORGANISM: Artificial Sequence
<220> FEATURE:
<223> OTHER INFORMATION: primer

<400> SEQUENCE: 21
gctgtagcca aatt                                                        14
```

```
<210> SEQ ID NO 22
<211> LENGTH: 16
<212> TYPE: DNA
<213> ORGANISM: Artificial Sequence
<220> FEATURE:
<223> OTHER INFORMATION: probe with homology to human sequence

<400> SEQUENCE: 22
agctcatttc ctggta                                                    16
```